(12) United States Patent
Gudas et al.

(10) Patent No.: US 11,191,755 B2
(45) Date of Patent: Dec. 7, 2021

(54) COMPOSITIONS AND METHODS FOR PROVIDING CARDIOPROTECTIVE EFFECTS

(71) Applicant: Cornell University, Ithaca, NY (US)

(72) Inventors: Lorraine J Gudas, New York, NY (US); Xiao-Han Tang, Staten Island, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 16/008,946

(22) Filed: Jun. 14, 2018

(65) Prior Publication Data

US 2018/0296545 A1    Oct. 18, 2018

Related U.S. Application Data

(63) Continuation-in-part of application No. 15/112,159, filed as application No. PCT/US2015/011820 on Jan. 16, 2015, which is a continuation-in-part of application No. PCT/US2014/012083, filed on Jan. 17, 2014.

(60) Provisional application No. 61/990,808, filed on May 9, 2014.

(51) Int. Cl.
| | |
|---|---|
| *A61K 31/4436* | (2006.01) |
| *A61K 31/426* | (2006.01) |
| *A61P 9/10* | (2006.01) |
| *A61P 9/06* | (2006.01) |
| *A61K 31/192* | (2006.01) |

(52) U.S. Cl.
CPC ........ *A61K 31/4436* (2013.01); *A61K 31/192* (2013.01); *A61K 31/426* (2013.01); *A61P 9/06* (2018.01); *A61P 9/10* (2018.01)

(58) Field of Classification Search
USPC ....................................................... 514/365
See application file for complete search history.

(56) References Cited

U.S. PATENT DOCUMENTS

| | | | |
|---|---|---|---|
| 5,576,349 | A | 11/1996 | Leaf et al. |
| 9,585,857 | B2 | 3/2017 | Gudas et al. |
| 2005/0171151 | A1 | 8/2005 | Yuan et al. |
| 2008/0139842 | A1 | 6/2008 | Koichi et al. |
| 2009/0137671 | A1 | 5/2009 | Noa |
| 2014/0187504 | A1 | 7/2014 | Chaturvedi |
| 2015/0313842 | A1 | 11/2015 | Schuler et al. |
| 2017/0135964 | A1 | 5/2017 | Gudas |
| 2018/0296545 | A1 | 10/2018 | Gudas et al. |

FOREIGN PATENT DOCUMENTS

| | | |
|---|---|---|
| EP | 0 698 392 | 2/1996 |
| EP | 1224 178 B1 | 8/2003 |
| WO | WO 98/42340 | 10/1998 |
| WO | WO 98/48055 | 10/1998 |
| WO | WO 2005/094333 A2 | 10/2005 |
| WO | WO 2006/108008 | 12/2006 |
| WO | WO 2007/009083 A2 | 1/2007 |
| WO | WO 2011/163183 A2 | 12/2011 |
| WO | WO 2012/162698 | 11/2012 |
| WO | WO 2012/178108 A1 | 12/2012 |
| WO | WO 2014/113695 | 7/2014 |

OTHER PUBLICATIONS

Paiva (Retinoic Acid Supplementation Attenuates Ventricular Remodeling after Myocardial Infarction in Rats, American Society for Nutrition, 2005, pp. 2326-2328).*
International Search Report for corresponding application No. PCT/US2015/011820 dated May 6, 2015.
Zabali et al. "Effecta of Vitamin A and insulin on the antioxidative state of diabetic rat heart a comparison study with combination tratment" Cell Biochmistry and Function, Jun. 2002, vol. 20 pp. 75-80.
Abahusain et al. "Retinal, a-tocopherol and carotenoids in diabetes" European Jornal of Clinical Nutrition, Aug. 1999, vol. 53 pp. 630-635 entire document.
Tsin et al. "Vitamin A Homeostasis in the Diabetic Rat" Journal of Clinical Biochemistry and Nutrition 1993, vol. 15, pp. 23-31 entire document.
European Search Report for corresponding application No. 15737537.9 dated Sep. 25, 2017.
Lund B W et al: "Discovery of a potent, orally available, and isoform-selective retinoic acid beta2 Receptor Agonist" Journal Of Medicinal Chemistry. American Chemical Society.vol. 48. No. 24. Apr. 11, 2005 (Apr. 11, 2005). pp. 7517-7519. XP002411145.
Miwako Ishido et al: "Oral Administration 1.4.6.9 of Synthetic Retinoid Am80 Inhibits The Development of Type 1 Diabetes In X.P A Non-Obese Diabetic (NOD) Mice.". Biological & Pharmaceutical Bulletin Jan. 2009. vol. 32. No. 1. Jan. 2009 (Jan. 2009). pp. 157-159. XP002773750. ISSN: 0918-6158.
Douguet D et al: "Quantitative 1-10 Structure-Activity Relationship Studies of Rar Alpha, Beta, Gamma Retinoid Agonists", Quantitative Structure-Activity Relationships, VCH Publishers, Deerfield Beach, FL, US, vol. 18, No. 2, Jan. 1, 1999 (Jan. 1, 1999), pp. 107-123, XP000957375, ISSN: 0931-8771.
Office Action from corresponding Canadian Application No. 2,937,107 dated Mar. 12, 2018.
Office Action from corresponding Chinese Application No. 201580012615.9 dated Aug. 13, 2018.

(Continued)

*Primary Examiner* — Kathrien A Cruz
(74) *Attorney, Agent, or Firm* — Mark S. Cohen; Pearl Cohen Zedek Latzer Baratz LLP

(57) ABSTRACT

The invention provides compositions and methods for providing a cardioprotective effect in a subject. Specifically, the invention provides compositions and methods for treating cardiovascular ailments, for example, ischemia/reperfusion (I/R) injury, cardiac arrhythmias, oxidative stress, or cardiac failure by administering a retinoic acid receptor-beta (RARβ) agonist.

13 Claims, 6 Drawing Sheets

(56) References Cited

OTHER PUBLICATIONS

Savitha Subramanian "Increased levels of invariant natural killer T lymphocytes worsens metabolic abnormalities and atherosclerosis in obese mice" The abstract, paragraph 2 in the right column on p. 2833 and paragraph 2 in the left column on p. 2835. Journal of Lipid Research, vol. 54 Nov. 30, 2013.

Guariguata L, Whiting D, Weil C, Unwin N. The International Diabetes Federation diabetes atlas methodology for estimating global and national prevalence of diabetes in adults. Diabetes research and clinical practiceDec. 2011;94(3):322-32.

Whiting DR, Guariguata L, Weil C, Shaw J. IDF diabetes atlas: global estimates of the prevalence of diabetes for 2011 and 2030. Diabetes research and clinical practice. [Research Support, Non-U. S. Gov't], Dec. 2011;94(3):311-21.

Huang ES, Basu A, O'Grady M, Capretta JC. Projecting the future diabetes population size and related costs for the U.S. Diabetes Care. [Research Support, N.I.H., Extramural Research Support, Non-U.S. Gov't], Dec. 2009;32(12):2225-9.

Oliver-Krasinski JM, Stoffers DA. On the origin of the beta cell. Genes & development. [Research Support, N.I.H., Extramural Review], Aug. 1, 2008 ;22(15):1998-2021.

Waldron-Lynch F, Herold KC. Immunomodulatory therapy to preserve pancreatic betacell function in type 1 diabetes. Nature reviews Drug discovery. [Review]. Jun. 2011;10(6):439-52.

Waldron-Lynch F, von Herrath M, Herold KC. Towards a curative therapy in type 1 diabetes: remission of autoimmunity, maintenance and augmentation of beta cell mass. Novartis Foundation symposium 2008; 292:146-55; discussion 55-8, 202-3.

Charbonnel B, Penfornis A, Varroud-Vial M, Kusnik-Joinville O, Detournay B. Insulin therapy for diabetes mellitus: Treatment regimens and associated costs. Diabetes & metabolismDec. 13, 2011.

Soria B, Andreu E, Berná G, Fuentes E, Gil A, León-Quinto T, Martín F, Montanya E, Nadal A, Reig JA, Ripoll C, Roche E, Sanchez-Andrés JV, Segura J. Engineering pancreatic islets. Pflügers Archiv—European Journal of Physiology2000;440(1):1-18.

Zaret KS, Grompe M. Generation and regeneration of cells of the liver and pancreas. Science. [Research Support, N.I.H., Extramural Research Support, Non-U.S. Gov't Review], Dec. 5, 2008;322(5907): 1490-4.

Weir GC, Cavelti-Weder C, Bonner-Weir S. Stem cell approaches for diabetes: towards beta cell replacement. Genome medicine2011;3(9):61.

Sui J, Mehta M, Shi B, Morahan G, Jiang FX. Directed Differentiation of Embryonic Stem Cells Allows Exploration of Novel Transcription Factor Genes for Pancreas Development. Stem cell reviewsJan. 26, 2012;1(1):1-10.

Ben-Yehudah A, White C, Navara CS, Castro CA, Ize-Ludlow D, Shaffer B, Sukhwani M, Mathews CE, Chaillet JR, Witchel SF. Evaluating protocols for embryonic stem cell differentiation into insulin-secreting beta-cells using insulin II-GFP as a specific and noninvasive reporter. Cloning Stem CellsJun. 11, 2009(2):245-57.

Blyszczuk P, Czyz J, Kania G, Wagner M, Roll U, St-Onge L, Wobus AM. Expression of Pax4 in embryonic stem cells promotes differentiation of nestin-positive progenitor and insulin-producing cells. Proc Natl Acad Sci U S A. [Research Support, Non-U.S. Gov't], Feb. 4, 2003;100(3):998-1003.

Borowiak M, Maehr R, Chen S, Chen AE, Tang W, Fox JL, Schreiber SL, Melton DA. Small molecules efficiently direct endodermal differentiation of mouse and human embryonic stem cells. Cell Stem CellApr. 3, 2009;4(4):348-58.

D'Amour KA, Bang AG, Eliazer S, Kelly OG, Agulnick AD, Smart NG, Moorman MA, Kroon E, Carpenter MK, Baetge EE. Production of pancreatic hormone-expressing endocrine cells from human embryonic stem cells. Nat Biotechnol. [Research Support, Non-U.S. Gov't], Nov. 2006;24(11):1392-401.

Kroon E, Martinson LA, Kadoya K, Bang AG, Kelly OG, Eliazer S, Young H, Richardson M, Smart NG, Cunningham J, Agulnick AD, D'Amour KA, Carpenter MK, Baetge EE. Pancreatic endoderm derived from human embryonic stem cells generates glucoseresponsive insulin-secreting cells in vivo. Nat Biotechno lApr. 26, 2008(4):443-52.

Micallef SJ, Janes ME, Knezevic K, Davis RP, Elefanty AG, Stanley EG. Retinoic acid induces Pdx1-positive endoderm in differentiating mouse embryonic stem cells. DiabetesFeb. 2005;54(2):301-5.

Laursen KB, Wong PM, Gudas LJ. Epigenetic regulation by RARalpha maintains ligand-independent transcriptional activity. Nucleic acids research Jan. 2012;40(1):102-15.

Jaramillo M, Banerjee I. Endothelial cell co-culture mediates maturation of human embryonic stem cell to pancreatic insulin producing cells in a directed differentiation approach. J Vis Exp2012(61).

Chen Y, Pan FC, Brandes N, Afelik S, Solter M, Pieler T. Retinoic acid signaling is essential for pancreas development and promotes endocrine at the expense of exocrine cell differentiation in Xenopus. Developmental biology. [Comparative Study Research Support, Non-U.S. Gov't], Jul. 1, 2004;271(1):144-60.

Ostrom M, Loffler KA, Edfalk S, Selander L, Dahl U, Ricordi C, Jeon J, Correa-Medina M, Diez J, Edlund H. Retinoic acid promotes the generation of pancreatic endocrine progenitor cells and their further differentiation into beta-cells. PLoS One. [Research Support, Non-U.S. Gov't], 2008;3(7):e2841.

Matthews KA, Rhoten WB, Driscoll HK, Chertow BS. Vitamin A deficiency impairs fetal islet development and causes subsequent glucose intolerance in adult rats. The Journal of nutrition. [Research Support, U.S. Gov't, P.H.S.]. Aug. 2004;134(8):1958-63.

Chertow BS, Blaner WS, Baranetsky NG, Sivitz WI, Cordle MB, Thompson D, Meda P. Effects of vitamin A deficiency and repletion on rat insulin secretion in vivo and in vitro from isolated islets. J Clin Invest. [In Vitro Research Support, Non-U.S. Gov't Research Support, U.S. Gov't, P.H.S.]. Jan. 1987;79(1):163-9.

Dodge R, Loomans C, Sharma A, Bonner-Weir S. Developmental pathways during in vitro progression of human islet neogenesis. Differentiation. [Research Support, N.I.H., Extramural Research Support, Non-U.S. Gov't], Feb. 2009;77(2):135-47.

Dolle P, Ruberte E, Leroy P, Morriss-Kay G, Chambon P. Retinoic acid receptors and cellular retinoid binding proteins. I. A systematic study of their differential pattern of transcription during mouse organogenesis. Development. [Research Support, Non-U.S. Gov't], Dec. 1990;110(4):1133-51.

Ghyselinck NB, Dupe V, Dierich A, Messaddeq N, Garnier JM, Rochette-Egly C, Chambon P, Mark M. Role of the retinoic acid receptor beta (RARp) during mouse development. The International journal of developmental biology. [Research Support, Non-U.S. Gov't Research Support, U.S. Gov't, P.H.S.]. Jun. 1997;41(3):425-47.

Martinez-Ceballos E, Gudas LJ. Hoxa1 is required for the retinoic acid-induced differentiation of embryonic stem cells into neurons. Journal of neuroscience research. [Research Support, N.I.H., Extramural]. Oct. 2008;86(13):2809-19.

Martinez-Ceballos E, Chambon P, Gudas LJ. Differences in gene expression between wild type and Hoxa1 knockout embryonic stem cells after retinoic acid treatment or leukemia inhibitory factor (LIF) removal. The Journal of biological chemistry. [Research Support, N.I.H., Extramural Research Support, U.S. Gov't, P.H.S.]. Apr. 22, 2005;280(16):16484-98.

Benoit YD, Lussier C, Ducharme PA, Sivret S, Schnapp LM, Basora N, Beaulieu JF. Integrin alpha8beta1 regulates adhesion, migration and proliferation of human intestinal crypt cells via a predominant RhoA/ROCK-dependent mechanism. Biology of the cell / under the auspices of the European Cell Biology Organization. [Research Support, Non-U.S. Gov't], Dec. 2009;101(12):695-708.

Auclair BA, Benoit YD, Rivard N, Mishina Y, Perreault N. Bone morphogenetic protein signaling is essential for terminal differentiation of the intestinal secretory cell lineage. GastroenterologySep. 2007; 133(3):887-96.

Yoshino J, Mills KF, Yoon MJ, Imai S. Nicotinamide mononucleotide, a key NAD(+) intermediate, treats the pathophysiology of diet- and age-induced diabetes in mice. Cell MetabOct. 5, 2011;14(4):528-36.

Spokoini R, Kfir-Erenfeld S, Yefenof E, Sionov RV. Glycogen synthase kinase-3 plays a central role in mediating glucocorticoid-induced apoptosis. Mol Endocrinol Jun. 2010;24(6):1136-50.

(56) References Cited

OTHER PUBLICATIONS

Yamaguchi TP, Takada S, Yoshikawa Y, Wu N, McMahon Ap. T (Brachyury) is a direct target of Wnt3a during paraxial mesoderm specification. Genes & developmentDec. 15, 1999;13(24):3185-90.
Otonkoski T, Beattie GM, Maliy MI, Ricordi C, Hayek A. Nicotinamide is a potent inducer of endocrine differentiation in cultured human fetal pancreatic cells. J Clin InvestSep. 1993;92(3):1459-66.
Lumelsky N, Blondel O, Laeng P, Velasco I, Ravin R, McKay R. Differentiation of embryonic stem cells to insulin-secreting structures similar to pancreatic islets. Science. [Research Support, Non-U.S. Gov't], May 18, 2001;292(5520):1389-94.
Marchand M, Schroeder IS, Markossian S, Skoudy A, Negre D, Cosset FL, Real P, Kaiser C, Wobus AM, Savatier P. Mouse ES cells over-expressing the transcription factor NeuroD1 show increased differentiation towards endocrine lineages and insulinexpressing cells. The International journal of developmental biology. [Research Support, Non-U.S. Gov't], 2009;53(4):569-78.
Langton S, Gudas LJ. CYP26A1 knockout embryonic stem cells exhibit reduced differentiation and growth arrest in response to retinoic acid. Developmental biology. [Research Support, N.I.H., Extramural Research Support, U.S. Gov't, Non-P.H.S.]. Mar. 15, 2008;315(2):331-54.
Soria B. In-vitro differentiation of pancreatic beta-cells. DifferentiationOct. 2001;68(4-5):205-19.
Van Hoof D, D'Amour KA, German MS. Derivation of insulin-producing cells from human embryonic stem cells. Stem cell research. [Research Support, Non-U.S. Gov't Review], Sep.-Nov. 2009;3(2-3):73-87.
Bernardo AS, Hay CW, Docherty K. Pancreatic transcription factors and their role in the birth, life and survival of the pancreatic beta cell. Mol Cell EndocrinolNov. 6, 2008;294(1-2):1-9.
Kashyap V, Rezende NC, Scotland KB, Shaffer SM, Persson JL, Gudas LJ, Mongan NP. Regulation of stem cell pluripotency and differentiation involves a mutual regulatory circuit of the NANOG, OCT4, and SOX2 pluripotency transcription factors with polycomb repressive complexes and stem cell microRNAs. Stem cells and developmentSep. 18, 2009;(7):1093-108.
Rukstalis JM, Habener JF. Neurogenin3: a master regulator of pancreatic islet differentiation and regeneration. IsletsNov.-Dec. 2009;1(3):177-84.
Gosmain Y, Katz LS, Masson MH, Cheyssac C, Poisson C, Philippe J. Pax6 is crucial for beta-cell function, insulin biosynthesis, and glucose-induced insulin secretion. Mol Endocrinol. [Research Support, Non-U.S. Gov't], Apr. 2012;26(4):696-709.
Ahlgren U, Pfaff SL, Jessell TM, Edlund T, Edlund H. Independent requirement for ISL1 in formation of pancreatic mesenchyme and islet cells. Nature. [Research Support, Non-U.S. Gov't], Jan. 16, 1997;385(6613):257-60.
Naujok O, Francini F, Picton S, Bailey CJ, Lenzen S, Jorns A. Changes in gene expression and morphology of mouse embryonic stem cells on differentiation into insulin-producing cells in vitro and in vivo. Diabetes Metab Res RevJul. 25, 2009(5):464-76.
Gasa R, Mrejen C, Leachman N, Otten M, Barnes M, Wang J, Chakrabarti S, Mirmira R, German M. Proendocrine genes coordinate the pancreatic islet differentiation program in vitro. Proc Natl Acad Sci U S ASep. 7, 2004;1 01 (36):13245-50.
Steiner DF, Cunningham D, Spigelman L, Aten B. Insulin biosynthesis: evidence for a precursor. ScienceAug. 11, 1967;157(3789):697-700.
Daly ME, Vale C, Walker M, Littlefield A, Alberti KG, Mathers JC. Acute effects on insulin sensitivity and diurnal metabolic profiles of a high-sucrose compared with a high-starch diet. Am J Clin NutrJun. 1998;67(6):1186-96.
Cryer PE, Axelrod L, Grossman AB, Heller SR, Montori VM, Seaquist ER, Service FJ. Evaluation and management of adult hypoglycemic disorders: an Endocrine Society Clinical Practice Guideline. The Journal of clinical endocrinology and metabolismMar. 2009;94(3):709-28.
Cai J, Yu C, Liu Y, Chen S, Guo Y, Yong J, Lu W, Ding M, Deng H. Generation of homogeneous PDX1(+) pancreatic progenitors from human ES cell-derived endoderm cells. J Mol Cell Biol. [Research Support, Non-U.S. Gov't], Feb. 2010;2(1):50-60.
Jonsson J, Carlsson L, Edlund T, Edlund H. Insulin-promoter-factor 1 is required for pancreas development in mice. NatureOct. 13, 1994;371(6498):606-9.
Fujimoto K, Polonsky KS. Pdx1 and other factors that regulate pancreatic beta-cell survival. Diabetes, obesity & metabolismNov. 2009;11 Suppl 4:30-7.
Dalgin G, Ward AB, Hao Ie T, Beattie CE, Nechiporuk A, Prince VE. Zebrafish mnx1 controls cell fate choice in the developing endocrine pancreas. DevelopmentNov. 2011;138(21):4597-608.
Vetere A, Marsich E, Di Piazza M, Koncan R, Micali F, Paoletti S. Neurogenin3 triggers beta-cell differentiation of retinoic acid-derived endoderm cells. The Biochemical journalMay 1, 2003;371 (Pt 3):831-41.
Dohrmann C, Gruss P, Lemaire L. Pax genes and the differentiation of hormone producing endocrine cells in the pancreas. Meeh DevMar. 15, 2000;92(1):47-54.
American Diabetes A. Diagnosis and classification of diabetes mellitus. Diabetes CareJan. 2005;28 Suppl 1:S37-42.
Del Prato S, Marchetti P. Beta- and alpha-cell dysfunction in type 2 diabetes. Horm Metab ResNov.-Dec. 2004;36(11-12):775-81.
Riserus U, Willett WC, Hu FB. Dietary fats and prevention of type 2 diabetes. Prog Lipid ResJan. 2009;48(1):44-51.
Sirchia SM, Ren M, Pili R, Sironi E, Somenzi G, Ghidoni R, Toma S, Nicolo G, Sacchi N. Endogenous reactivation of the RARβ2 tumor suppressor gene epigenetically silenced in breast cancer. Cancer researchMay 1, 2002;62(9):2455-61.
Youssef EM, Estecio MR, Issa JP. Methylation and regulation of expression of different retinoic acid receptor beta isoforms in human colon cancer. Cancer Biol TherJan. 2004;3(1):82-6.
House MG, Herman JG, Guo MZ, Hooker CM, Schulick RD, Lillemoe KD, Cameron JL, Hruban RH, Maitra A, Yeo CJ. Aberrant hypermethylation of tumor suppressor genes in pancreatic endocrine neoplasms. Ann SurgSep. 2003;238(3):423-31; discussion 31-2.
Sato N, Fukushima N, Hruban RH, Goggins M. CpG island methylation profile of pancreatic intraepithelial neoplasia. Mod PatholMar. 2008;21(3):238-44.
Volkmar M, Dedeurwaerder S, Cunha DA, Ndlovu MN, Defrance M, Deplus R, Calonne E, Volkmar U, Igoillo-Esteve M, Naamane N, Del Guerra S, Masini M, Bugliani M, Marchetti P, Cnop M, Eizirik DL, Fuks F. DNA methylation profiling identifies epigenetic dysregulation in pancreatic islets from type 2 diabetic patients. EMBO JMar. 21, 2012;31(6):1405-26.
Lund, B. W.; Piu, F.; Gauthier, N. K.; Eeg, A.; Currier, E.; Sherbukhin,V.; Brann, M. R.; Hacksell, U.; Olsson, R. Discovery of a Potent,Orally Available, and Isoform-Selective Retinoic Acid beta2 Receptor Agonist. J. Med. Chem. 2005, 48, 7517-7519.
Vivat-Hannah V et al., Synergistic Cytotoxicity Exhibited by Combination Treatment of Selective Retinoid Ligands with Taxol (Paclitaxel). Cancer Res. 2001, 61, 8703-8711.
Millikan LE, Adapalene: an update on newer comparative studies between the various retinoids. Int.J.Dermatol..2000, 39, 784-88.
Chen JY et al. (1995) RAR-specific agonist/antagonists which dissociate transactivation and AP1 transrepression inhibit anchorage-independent cell proliferation. EMBO J. 1995, 14, 1187-97.
Lazo M, Hernaez R, Eberhardt MS, Bonekamp S, Kamel I, Guallar E, Koteish A, Brancati FL, Clark JM.Prevalence of nonalcoholic fatty liver disease in the United States: the Third National Health and Nutrition Examination Survey, 1988-1994. Am J Epidemiol. 2013; 1:38-45.
Loomba R, Sanyal AJ. The global NAFLD epidemic. Nat Rev Gastroenterol Hepatol. 2013;11:686-90.
Baffy G, Brunt EM, Caldwell SH.Hepatocellular carcinoma in non-alcoholic fatty liver disease: an emerging menace. J Hepatol. 2012; 6:1384-91.
Reeves HL, Friedman SL. Activation of hepatic stellate cells-a key issue in liver fibrosis. Front Biosci. 2002; 7:808-26.
Puche JE, Saiman Y, Friedman SL. Hepatic stellate cells and liver fibrosis. Compr Physiol. 2013;4):1473-92.

(56) References Cited

OTHER PUBLICATIONS

Geerts, A. History, heterogeneity, developmental biology, and functions of quiescent hepatic stellate cells. Semin. Liver Dis. 2001;21:311-335.
Brun PJ, Yang KJ, Lee SA, Yuen JJ, Blaner WS. Retinoids: Potent regulators of metabolism. Biofactors. 2013 2):151-63.
(CDC) CfDCaP. Vital signs: prevalence, treatment, and control of high levels of low-density lipoprotein cholesterol-United States, 1999-2002 and 2005-200. MMWR Morb Mortal Wkly Rep. 2011;60(4):109-14. PubMed PMID: 21293326.
Martin SS, Abd TT, Jones SR, Michos ED, Blumenthal RS, Blaha MJ. 2013 American Cholesterol Treatment Guideline: What Was Done Well and What Could Be Done Better. J Am Coll Cardiol. 2014. doi: 10.1016/j.jacc.2014.02.578. PubMed PMID: 24681146.
Mampuya WM, Frid D, Rocco M, Huang J, Brennan DM, Hazen SL, Cho L. Treatment strategies in patients with statin intolerance: the Cleveland Clinic experience. Am Heart J. 2013;166(3):597-603. doi: 10.1016/j.ahj.2013.06.004. PubMed PMID: 24016512.
Tang XH, Gudas LJ. Retinoids, retinoic acid receptors, and cancer. Annu Rev Pathol. 2011;6:345-64. doi: 10.1146/annurev-pathol-011110-130303. PubMed PMID: 21073338.
Baldwin HE, Highland M, Kendall C, Mays DA, Grossman R, Hewburger J. 40 years of topical tretinoin use in review. J Drugs Dermatol. 2013;12(6):638-42. PubMed PMID: 23839179.
Ellis CH, Swanson HA, Grekin RC, Goldstein HG, Bassett DR, Anderson TF, Voorhees JJ. Etretinate therapy causes increases in lipid levels in patients with psoriasis. Arch Dermatol. 1982;118(8):559-62. PubMed PMID: 7103524.
Lyons F, Laker MF, Marsden JR, Manuel R, Shuster S. Effect of oral 13-cis-retinoic acid on serum lipids. Br J Dermatol. 1982;107(5):591-5. PubMed PMID: 6215057.
Marsden J. Hyperlipidaemia due to isotretinoin and etretinate: possible mechanisms and consequences. Br J Dermatol. 1986;114(4):401-7. PubMed PMID: 3516195.
Barth JH, Macdonald-Hull SP, Mark J, Jones RG, Cunliffe WJ. Isotretinoin therapy for acne vulgaris: a re-evaluation of the need for measurements of plasma lipids and liver function tests. Br J Dermatol. 1993;129(6):704-7. PubMed PMID: 8286255.
Amengual J, Ribot J, Bonet ML, Palou A. Retinoic acid treatment enhances lipid oxidation and inhibits lipid biosynthesis capacities in the liver of mice. Cell Physiol Biochem. 2010;25(6):657-66. doi: 10.1159/000315085. PubMed PMID: 20511711.
Kim SC, Kim CK, Axe D, Cook A, Lee M, Li T, Smallwood H, Chiang JY, Hardwick JP, Moore DD, Lee YK. All-trans-retinoic acid ameliorates hepatic steatosis in mice by a novel transcriptional cascade. Hepatology. 2013. doi: 10.1002/hep.26699. PubMed PMID: 24038081.
Thacher SM, Vasudevan J, Chandraratna RA. Therapeutic applications for ligands of retinoid receptors. Curr Pharm Des. 2000;6(1):25-58. PubMed PMID: 10637371.
Laursen KB, Mongan NP, Zhuang Y, Ng MM, Benoit YD, Gudas LJ. Polycomb recruitment attenuates retinoic acid-induced transcription of the bivalent NR2F1 gene. Nucleic Acids Res. 2013;41(13):6430-43. doi: 10.1093/nar/gkt367. PubMed PMID: 23666625.
Buchovercky CM, Turley SD, Brown HM, Kyle SM, McDonald JG, Liu B, Pieper AA, Huang W, Katz DB, Russell DW, Shendure J, Justice MY. A suppressor screen in Mecp2 mutant mice implicates cholesterol metabolism in Rett syndrome. Nature Genetics. Sep. ;45(9):1013-20; Epub Jul. 28, 2013.
Justice, MJ, Public Research Seminar (A genetic suppressor screen in mice reveals that lipid metabolism is a therapeutic target for Rett Syndrome) at Sloan Kettering Institute, May 1, 2014.
International Search Report for corresponding application No. PCT/US19/37110 dated Sep. 5, 2019.
Bilbija, D et al., Retinoic Acid Signalling Is Activated in the Postischemic Heart and May Influence Remodelling, PLoS ONE 7(9), pp. 1-9,2012; p. 2, col. 1, second paragraph.
Zhu, Z et al., All-Trans Retinoic Acid Ameliorates Myocardiallschemia/Reperfusion Injury by Reducing Cardiomyocyte Apoptosis, PLoS ONE 10(7), pp. 1-15,2015; abstract; p. 6, second paragraph; p. 7, figure 1; p. 10, fourth paragraph.
L Ymperopoulos, A et al., The Adrenergic Nervous System in Heart Failure: Pathophysiology and Therapy, Circulation Research 113(6), pp. 1-28,2013; abstract; p. 2, fourth paragraph; p. 3, second paragraph; p. 7, first paragraph.
Newton, GE et al., Acute Effects of Betal-Selective and Nonselective Beta-Adrenergic Receptor Blockade on Cardiac Sympathetic Activity in Congestive Heart Failure, Circulation 94,pp. 353-358, 1996; abstract.
Office Action from corresponding European Application No. 15737537.9 dated Mar. 18, 2020.
Reiner Z. "Managing the residual Cardiovascular disease risk associated with HDL-cholesterol and triglycerides in Statin-treated patients: A clinical update". Nutrition, Metabolism & Cardiovascular Diseases (2013) 23, 23:799-807.
Office Action corresponding U.S. Appl. No. 15/112,159 dated Dec. 28, 2020.
Husmann et al., "Antagonism between Retinoic Acid Receptors" Mol. & Cell. Biol. (Aug. 1991) 11:4097-4103.

* cited by examiner

COMPOSITIONS AND METHODS FOR PROVIDING CARDIOPROTECTIVE EFFECTS

CROSS-REFERENCE TO RELATED APPLICATIONS

This is a continuation-in part application of U.S. patent application Ser. No. 15/112,159, filed Jul. 15, 2016, which is a National Phase Application of PCT International Patent Application PCT/US15/11820, filed Jan. 16, 2015, which is a continuation-in-part of PCT International Patent Application PCT/US14/12083, filed Jan. 17, 2014 and also claims priority to and the benefit of U.S. Provisional Application 61/990,808, filed May 9, 2014. All applications above are incorporated by reference herein in their entirety.

GOVERNMENT FUNDING

This invention was made with Government support under Grant Number NIH R01 DK113088, awarded by the National Institutes of Health. The United States Government has certain rights in the invention.

FIELD OF THE INVENTION

The invention relates to compositions and methods for providing a cardioprotective effect in a subject. Specifically, the invention relates to compositions and methods for treating cardiovascular ailments, for example, ischemia/reperfusion (I/R) injury, cardiac arrhythmias, and cardiac failure by administering a retinoic acid receptor-beta (RARβ) agonist. These ailments are associated with the Type 2 Diabetes and hyperlipidemia that may also be treated with RARβ agonists.

BACKGROUND OF THE INVENTION

Early reperfusion of an occluded coronary artery after myocardial infarction can reduce infarct size, which contributes to preserving left ventricular contraction and preventing the onset of heart failure and other pathologies. However, reperfusion paradoxically can cause further cardiomyocyte death, which is generally known as myocardial ischemia/reperfusion (I/R) injury. Ischemic reperfusion injury is accompanied by severe arrhythmias, such as ventricular tachycardia (VT) and agonist (VF), which are significant causes of sudden death in patients with ischemic heart disease.

In the I/R heart, mast cells (MC) activation contributes significantly to arrhythmia generation. Reactive oxygen species (ROS), a class of highly reactive and unstable molecules, mainly generated in mitochondria. During reperfusion, a rise in ROS and toxic aldehyde production are responsible for MC degranulation; this is associated with the release of MC-derived active renin, the first step in the activation of a local renin-angiotensin system (RAS) in the heart, which is responsible for enhanced norepinephrine release and arrhythmias. Monoaminoxidases (MAO) are mitochondrial enzymes responsible for catecholamine catabolism, which generates hydrogen peroxide, aldehyde, and ammonia as by-products, contributing to oxidative stress and ROS production in the heart. Since increased ROS production at the mitochondrial level exacerbates I/R injury, eliciting arrhythmias and left ventricular remodeling, numerous studies have explored therapeutic strategies such as antioxidants to counteract ROS production and oxidative responses, ultimately affording cardioprotection.

Vitamin A (retinol) and its metabolites and derivatives, collectively known as retinoids, are important lipophilic signaling molecules that play critical roles in controlling both vertebrate development and stem cell differentiation in the adult. The actions of retinoids, such as the potent, biologically active endogenous metabolite of vitamin A, all-trans retinoic acid (RA), are primarily mediated by binding to ligand-activated transcription factors, the retinoic acid receptors (RARs) α, β, and γ. When RARs bind the pan-agonist RA, they heterodimerize with retinoid X receptors (RXRs) α, β, and γ. Agonists that bind to different RAR receptors can be expected to have different effects because different RARs are known to have different biological functions. The RARs are expressed in the heart during development and in the adult, and RA signaling is active in the post-ischemic heart. The RA signaling pathway can reduce cardiac I/R injury and ROS production. RA also displayed protective effects against cardiac arrhythmias. Moreover, all-trans retinoic acid protected against doxorubicin-induced cardiotoxicity, in which oxidative stress and I/R-like damage are known to play a major role. Furthermore, supplementation with RA has been shown to prevent left ventricular (LV) dilatation and preserved ventricular function in rats with induced infarction. Conversely, in adult rats, vitamin A deficiency has been demonstrated to cause left ventricular dilatation that led to a major decrease in cardiac function. Loss of RARα specifically in mouse cardiomyocytes resulted in diastolic dysfunction from increased ROS.

Accordingly, there remains an unmet need for therapeutic compositions and treatment methods capable of preventing myocardial reperfusion injury and reducing myocardial infarct (MI) size, so as to preserve heart function (LV systolic function) and prevent the onset of heart failure in patients presenting with myocardial infarction at risk of myocardial ischemia/reperfusion (I/R) injury. There also exists an unfulfilled demand for improved methods for treatment of other cardiovascular ailments, such as chronic arrhythmias and cardiac failure, and more specifically to methods for providing a cardioprotective effect on a heart of a subject in need thereof.

SUMMARY OF THE INVENTION

In one aspect, the invention provides a method for providing a cardioprotective effect on a heart of a subject in need thereof, comprising administering to the subject a therapeutically effective amount of a retinoic acid receptor-beta (RARβ) agonist. In an exemplary embodiment, said RARβ agonist is AC261066.

In another aspect, the invention provides a method for reducing myocardial injury or ischemia/reperfusion (I/R) injury to a heart of a subject in need thereof, comprising administering to the subject a therapeutically effective amount of a retinoic acid receptor-beta (RARβ) agonist.

In an additional aspect, the invention provides a method for treating or alleviating a chronic arrhythmia in a subject in need thereof, comprising administering to the subject a therapeutically effective amount of a retinoic acid receptor-beta (RARβ) agonist.

In another aspect, the invention provides a method for treating a cardiac failure in a subject in need thereof, comprising administering to the subject a therapeutically effective amount of a retinoic acid receptor-beta (RARβ) agonist.

In a further aspect, the invention provides a pharmaceutical formulation comprising a therapeutically effective amount of a retinoic acid receptor-beta (RARβ) agonist and a pharmaceutically acceptable excipient.

Other features and advantages of the present invention will become apparent from the following detailed description examples and figures. It should be understood, however, that the detailed description and the specific examples, while indicating various embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1(A) graphically shows duration of reperfusion arrhythmias (VT/VF) in WT, ApoE$^{-/-}$ and ApoE$^{-/-}$+AC261066. FIG. 1(B) graphically shows overflows of NE in the first 6 minutes from the start of reperfusion in WT, untreated or treated with AC261066 (ApoE$^{-/-}$ and ApoE$^{-/-}$+AC261066, respectively). FIG. 1(C) shows a qualitative and quantitative representation of TTC staining in 2-mm-thick left ventricle slices collected at the end of reperfusion. Bars indicate infarcted slice areas as a percentage of total slice areas (Ai/Av %; means±SEM of independent experiments). Pale areas indicate I/R-injured tissue, while healthy tissue is colored in red. *, P<0.05; **, P<0.01, by unpaired t-test. Each open circle is one mouse.

FIG. 2(A) shows representative images of oxidative stress staining in ApoE$^{-/-}$ and ApoE$^{-/-}$+AC261066. Anti-malondialdehyde (MDA) stain in mouse heart frozen sections, the red arrow points to brown spots denoting MDA. Magnification: 200×, Scale bars: 50 μm. Two samples per group are shown. FIG. 2(B) is a graphic quantification of MDA levels in all fields. Six-eight representative areas of each heart section from 3-4 mice per group were photographed and analyzed. The quantification was carried out using ImageJ (NIH). Student's t test was used for statistical analysis (****P<0.0001).

FIG. 3(A) shows representative images of intact and degranulated cardiac mast cells (MC) in WT hearts subjected to ex-vivo I/R. FIG. 3(B) is a graphic quantification of MC degranulation in WT, ApoE$^{-/-}$ and ApoE$^{-/-}$+AC261066, calculated as a percentage of degranulated MC over total MC. *, P<0.05 by one-way ANOVA followed by Tukey's post-hoc test.

FIG. 4(A) shows duration of reperfusion arrhythmias (VT/VF) in WT, HFD and HFD+AC261066. FIG. 4(B) shows overflows of NE collected during 6 minutes from the start of reperfusion. FIG. 4(C) shows a qualitative and quantitative representation of TTC staining in 2-mm-thick left ventricle slices. Scale bar is 1 mm. Bars indicate means±SEM of independent experiments. Pale areas indicate I/R-injured tissue, while healthy tissue is colored in red. *, P<0.05; **, P<0.01, by unpaired Student's t-test.

FIG. 5(A) shows body weight of WT, ApoE$^{-/-}$, and AC261066-treated ApoE$^{-/-}$ mice at the time of the experiment (WT, n=7; ApoE$^{-/-}$, n=7, ApoE$^{-/-}$+AC261066, n=7). FIG. 5(B) shows blood levels of total cholesterol (light blue), triglycerides (yellow), HDL (black) and LDL (red; nd=not detectable in WT) in ApoE$^{-/-}$ and AC261066-treated ApoE$^{-/-}$ mice. Bars indicate means±SEM. *, P<0.05; , P<0.01; *, P<0.001 by one-way ANOVA followed by Tukey's post-hoc test.

DETAILED DESCRIPTION OF THE INVENTION

Figures 1A, 1B, 1C:
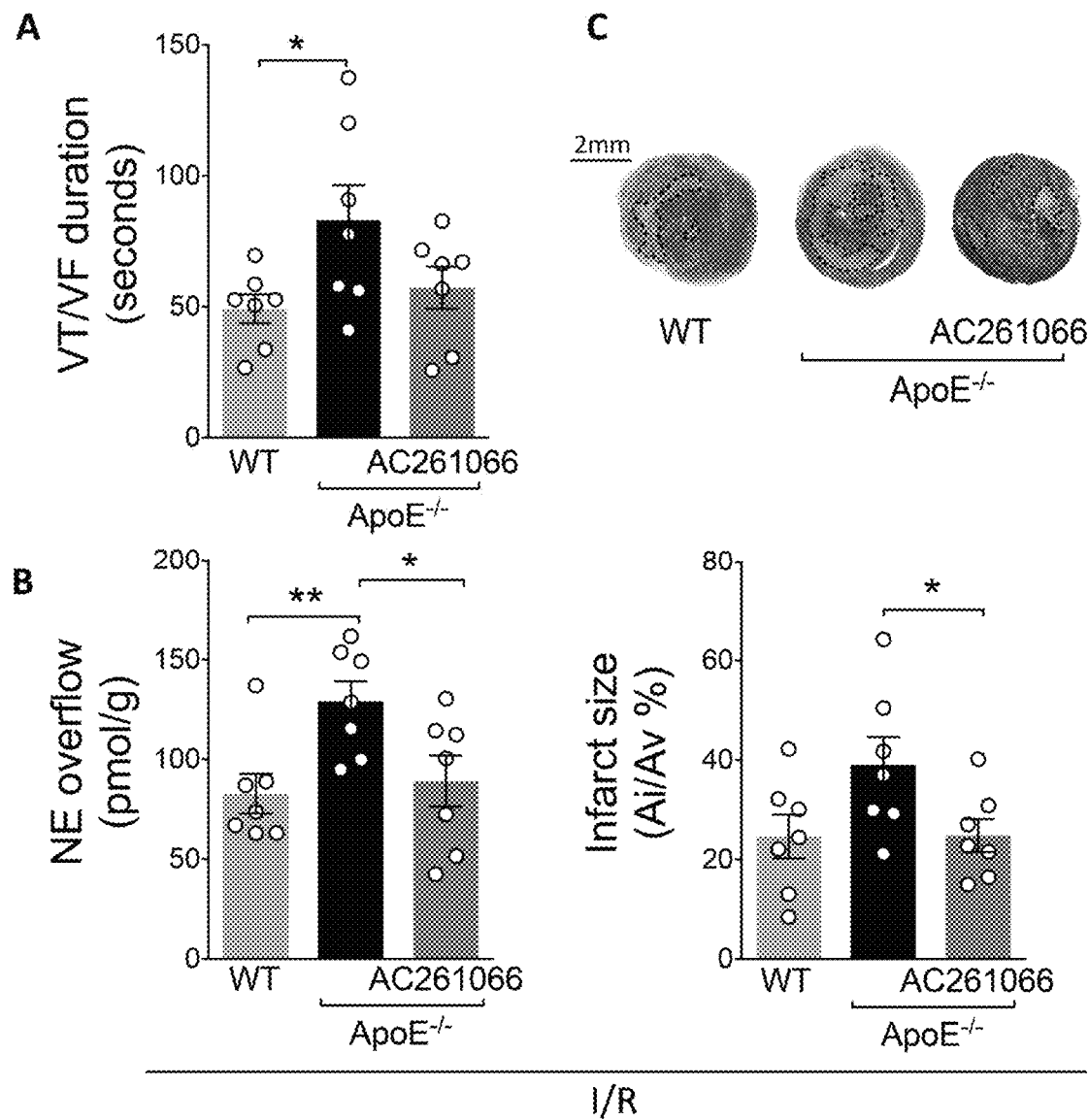
FIGS. 1(A)-1(C) illustrate that the RARβ$_2$ agonist AC261066 reduces NE overflows, alleviates reperfusion arrhythmias, and decreases infarct sizes in hearts isolated from ApoE$^{-/-}$ mice subjected to ex-vivo I/R. Mouse hearts were subjected to 40-minute global ischemia followed by 120-minute reperfusion (WT, n=7; ApoE$^{-/-}$, n=7, ApoE$^{-/-}$+AC261066, n=7).

The present subject matter may be understood more readily by reference to the following detailed description which forms a part of this disclosure. It is to be understood that this invention is not limited to the specific methods, products, conditions or parameters described and/or shown herein, and that the terminology used herein is for the purpose of describing particular embodiments by way of example only and is not intended to be limiting of the claimed invention.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality", as used herein, means more than one. When a range of values is expressed, another embodiment includes from the one particular and/or to the other particular value. Similarly, when values are expressed as approximations, by use of the antecedent "about," it is understood that the particular value forms another embodiment. All ranges are inclusive and combinable.

In the context of the present disclosure, by "about" a certain amount it is meant that the amount is within ±20% of the stated amount, or preferably within ±10% of the stated amount, or more preferably within ±5% of the stated amount.

As used herein, the terms "component," "composition," "composition of compounds," "compound," "drug," "pharmacologically active agent," "active agent," "therapeutic," "therapy," "treatment," or "medicament" are used interchangeably herein to refer to a compound or compounds or composition of matter which, when administered to a subject (human or animal) induces a desired pharmacological and/or physiologic effect by local and/or systemic action.

As used herein, the terms "treatment" or "therapy" (as well as different forms thereof) include preventative (e.g., prophylactic), curative or palliative treatment. As used herein, the term "treating" includes alleviating or reducing at least one adverse or negative effect or symptom of a condition, disease or disorder.

The term "ischemia" refers herein to an inadequate blood supply, including stopped blood flow, to heart muscle, that prevents the heart muscle tissue from receiving enough oxygen to keep it alive. The terms "ischemia-reperfusion injury", "reperfusion injury" and "reoxygenation injury" refer herein to tissue damage caused when the blood supply is returned to the tissue after a period of ischemia. The lack of oxygen and nutrients during ischemia creates a condition in which the restoration of circulation results in inflammation and oxidative damage through the induction of oxidative stress rather than (or along with) restoration of normal function.

The terms "subject," "individual," and "patient" are used interchangeably herein, and refer to an animal, for example a human, to whom treatment, including prophylactic treatment, with the pharmaceutical composition according to the present invention, is provided. The term "subject" as used herein refers to human and non-human animals. The terms "non-human animals" and "non-human mammals" are used interchangeably herein and include all vertebrates, e.g., mammals, such as non-human primates, (particularly higher primates), sheep, dog, rodent, (e.g. mouse or rat), guinea pig, goat, pig, cat, rabbits, cows, horses and non-mammals such as reptiles, amphibians, chickens, and turkeys.

As used herein, the terms "cardioprotective" effect and "cardioprotection" refer to and encompass methods of preserving the function and viability of cardiac muscle cells subjected to ischemia or to reperfusion injury, also called "ischemia-reperfusion injury" or "reoxygenation injury". Cardioprotection may be implemented before an ischemic event (preconditioning), during an ischemic event (preconditioning) and after the event and during reperfusion (postconditioning). Cardioprotective methods provided herein performed prior to an ischemic event may provide immediate onset of protection against myocardial infarction up to at least six weeks or longer against myocardial infarction. In various embodiments, administration of a retinoic acid receptor-beta (RARβ) agonist to a subject in need thereof, in particular administration of a RARβ2 agonist produces or exerts a cardioprotective effect, at a time period ranging from about 6 weeks to at least about one year, prior to a myocardial infarction in the subject.

Cardioprotection may be effected during an ischemic event to provide immediate onset of protection against myocardial infarction by attenuating an infarct size in the heart, diminishing coronary norepinephrine spillover during reperfusion of the heart, reducing oxidative damage, and/or alleviating reperfusion arrhythmias. The reperfusion arrhythmias comprise ventricular tachycardia and/or ventricular fibrillation. The ventricular tachycardia (VT) and/or ventricular fibrillation (VF) may be present when the subject has a heart disease, i.e., prior to a myocardial infarction in the subject.

The present invention relates to producing or providing a cardioprotective effect on a heart of a subject in need thereof, by administering to the subject a therapeutically effective amount of a retinoic acid receptor-beta (RARβ) agonist, in particular an RARβ$_2$ agonist. The invention also relates to treatment methods for reducing a myocardial injury, alleviating arrhythmias associated with or present during myocardial infarction, as well as treating cardiac ailments, including but not limited to chronic arrhythmia and cardiac failure in a subject in need thereof.

While not intending to be bound by any particular mechanism of operation, it is believed that the retinoic acid receptor-beta (RARβ) agonist, specifically an RARβ$_2$ agonist, administered according to the present invention effects or exerts cardioprotection by a reduction in oxidative stress and mast cell (MC) degranulation. Furthermore, it is believed that the reduction in myocardial injury and adrenergic activation, and the antiarrhythmic effects result from decreased formation of oxygen radicals and toxic aldehydes; oxygen radicals and toxic aldehydes are known to elicit the release of MC-derived renin, promoting the activation of local renin-angiotensin system (RAS) leading to enhanced NE release and reperfusion arrhythmias.

Various embodiments of the invention provide methods for producing cardioprotective effects (cardioprotection) and pharmaceutical formulations that comprise a retinoic acid receptor-beta (RARβ) agonist, more specifically, an RARβ$_2$ agonist. Such pharmaceutical formulations can be configured in various ways and in a variety of dosage forms, such as formulations for oral and peritoneal administration, to reduce oxidative stress and mast cell (MC) degranulation and/or to diminish coronary norepinephrine spillover during reperfusion of the heart.

As used herein, the terms "decrease", "reduce" and "diminish" are used interchangeably to refer to a negative change in the level, activity or function of a molecule, cell or organ. It is meant that the particular level, activity or function is lower by about 10%, about 25%, about 50%, about 75%, about 90%, about 1-fold, about 2-fold, about 5 fold, about 10-fold, about 25-fold, about 50-fold, or about 100 fold, or lower, when compared to a control.

As used herein, the terms "elevate", "increase", "improve" and "enhance" are used interchangeably to refer to a positive change in the level, activity or function of a molecule, cell or organ. It is meant that the particular level, activity or function is higher by about 10%, about 25%, about 50%, about 75%, about 90%, about 1-fold, about 2-fold, about 5 fold, about 10-fold, about 25-fold, about 50-fold, or about 100 fold, or higher, when compared to a control.

The retinoic acid receptor (RAR) is a type of nuclear receptor that is activated by both all-trans retinoic acid and 9-cis retinoic acid. There are three retinoic acid receptors (RAR), RARα, RARβ, and RARγ, encoded by the RARα, RARβ, RARγ genes, respectively. Each receptor isoform has several splice variants: four-for α, four-for β, and two-for γ.

RAR heterodimerizes with RXR and in the absence of ligand, the RAR/RXR dimer binds to hormone response elements known as retinoic acid response elements (RAREs) complexed with corepressor protein. Binding of agonist ligands to RAR results in dissociation of corepressor and recruitment of coactivator protein that, in turn, promotes transcription of the downstream target gene into mRNA and eventually protein.

The RARβ subtype consists of four known isoforms RARβ1, RARβ2, RARβ3 and RARβ4. The ligand binding domains of the four isoforms are identical, while the variation between the isoforms is located within the proximal N-terminus, which encompasses the ligand-independent activation domain (AF-1).

It has been reported that the ligand binding domain, i.e., AF-2, of a given RAR isotype cooperates with the AF-1 domain in a promoter context manner. The AF-2 domains are conserved between the isoforms, the AF-1 domains are not. Relying on RARβ (e.g., RARβ2) receptor-ligand crystal structure, various RARβ agonists have been designed and identified.

Known RARβ agonists, include but are not limited to, AC261066, AC55649, Tazarotene, Adapalene, 9-cis-retinoic acid, and TTNPB. AC261066 and AC55649 are highly-specific RARβ agonists. The term "highly-specific RARβ agonists" also include other agonists having a binding affinity similar to AC261066 or AC55649, e.g., at least 50% or greater, preferably 75% or greater, more preferably 90% or greater of the RARβ binding affinity of AC261066 or AC55649. The term "highly-specific RARβ2 agonists" include agonists having a binding affinity similar to AC261066 or AC55649, e.g., at least 50% or greater, preferably 75% or greater, more preferably 90% or greater of the RARβ2 binding affinity of AC261066 or AC55649. A highly-specific RARβ (e.g., RARβ2) agonist preferably has an affinity for RARβ (e.g., RARβ2) greater than 6.00 pEC50, more preferably greater than 6.50 pEC50, more preferably greater than 7.00 pEC50, more preferably greater than 7.50 pEC50, more preferably greater than 7.75 pEC50, and even more preferably greater than 8.00 pEC50.

RAR βagonists include the fluorinated alkoxythiazoles previously described, such as:

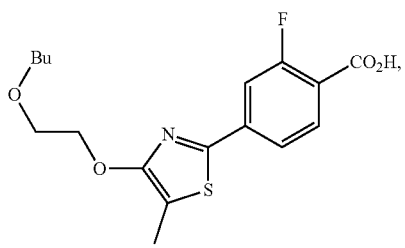

4'-Octyl[1,1'-biphenyl]-4-carboxylic acid (65), Adapalene (67), BMS-231973, BMS-228987, BMS-276393, BMS-209641 (66), BMS-189453{4-[(1E)-2-(5,6-Dihydro-5,5-dimethyl-8-phenyl-2-naphthalenyl)ethenyl]-benzoic acid} (68), CD2019 (6-[4-methoxy-3-(1-methylcyclohexyl)phenyl]naphthalene-2-carboxylic acid), compounds described in WO2008/064136 and WO2007009083, each of which is incorporated herein by reference in its entirety, and tazarotene (ethyl 6-[2-(4,4-dimethyl-3,4-dihydro-2H-1-benzothiopyran-6-yl)ethynyl] pyridine-3-carboxylate). Structures of some RAR βagonists are provided below:

AC261066:

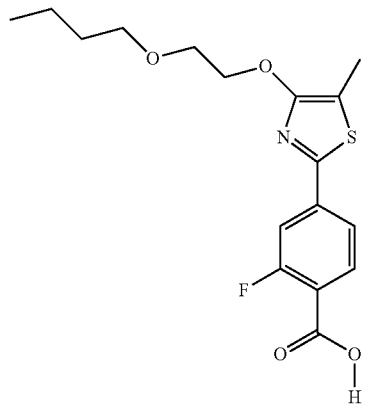

AC55649:

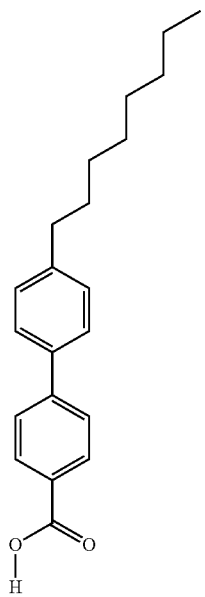

Tazarotene:

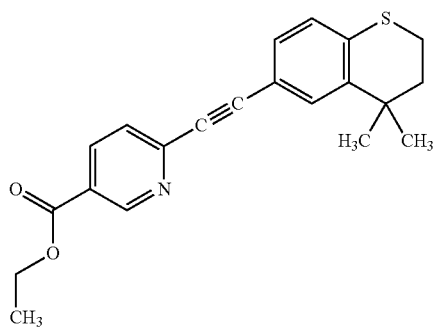

Adapalene:

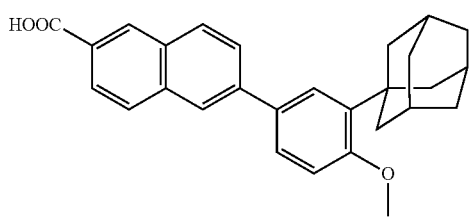

9-cis-retinoic acid:

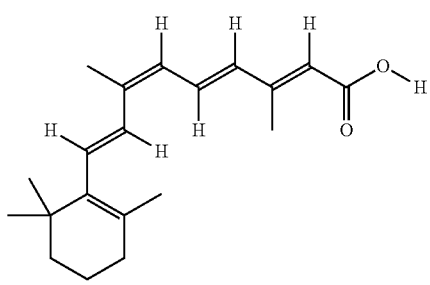

TTNPB:

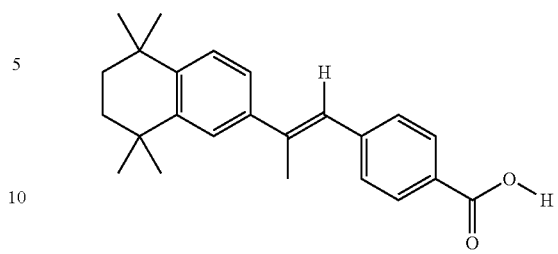

RARβ agonists also include those disclosed in published PCT patent application WO2008/064136, WO2007/009083 and published U.S. patent application US2009/0176837, each of which is incorporated herein by reference in its entirety. The highly specific RARβ agonists, e.g., AC261066 and AC55649, are highly isoform-selective agonists for the human RARβ2 receptors as described in Lund et al. (2005, J. Med. Chem., 48, 7517-7519), which is incorporated herein by reference in its entirety. In a particular embodiment, RARβ2 agonist is AC261066.

RARβ2 receptor agonist of the present invention may also be selected from the following compounds or an ester thereof:

1

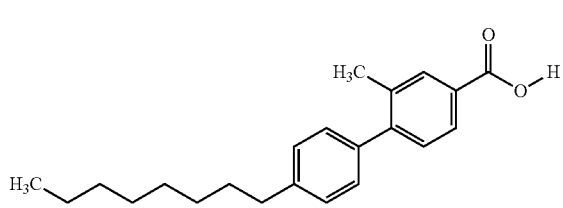

2

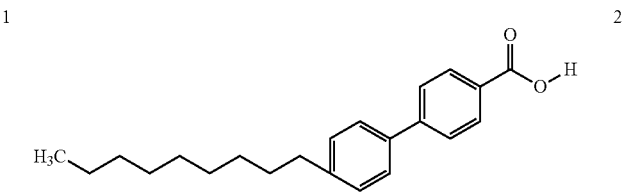

3

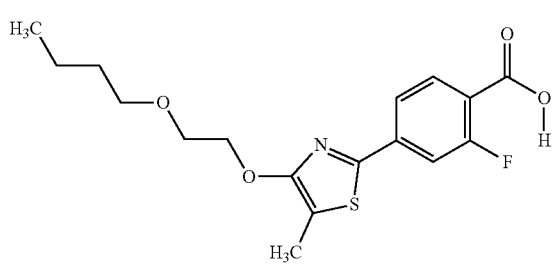

4

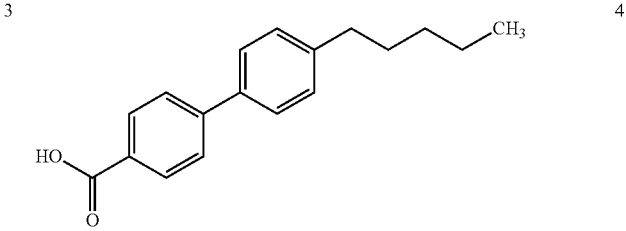

6

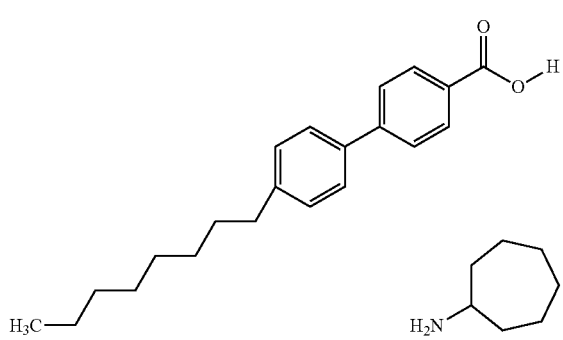

8

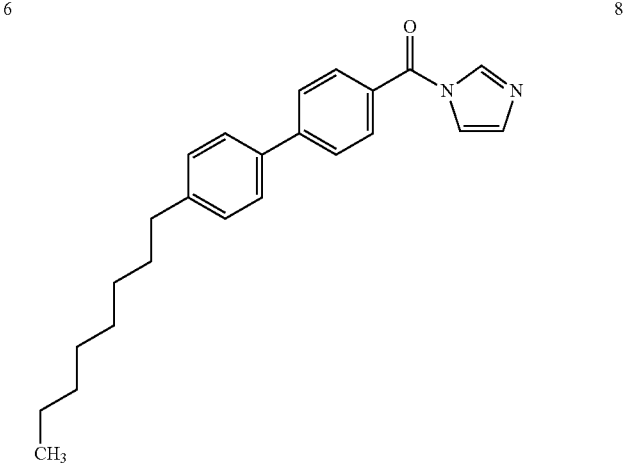

-continued
9
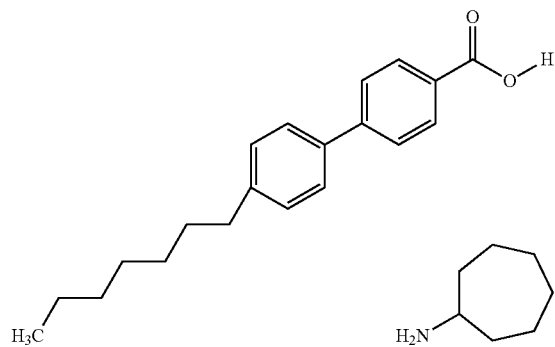
10
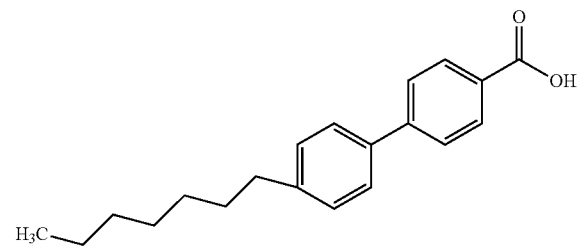
11
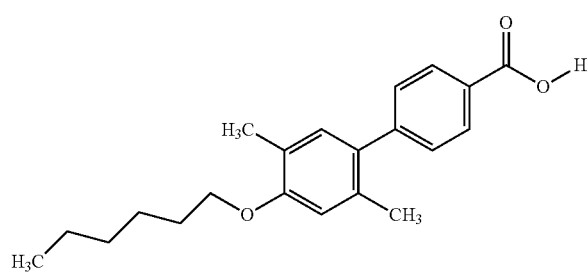
12
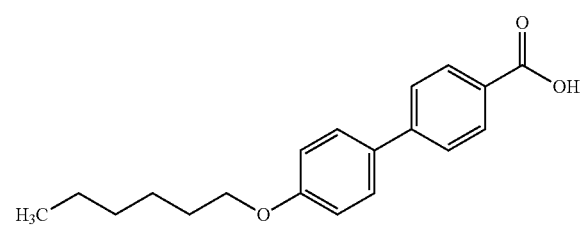
13
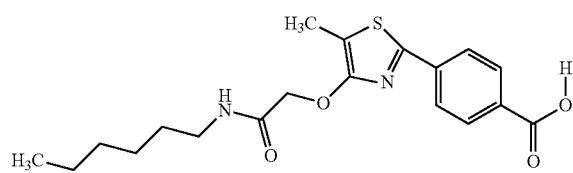
15
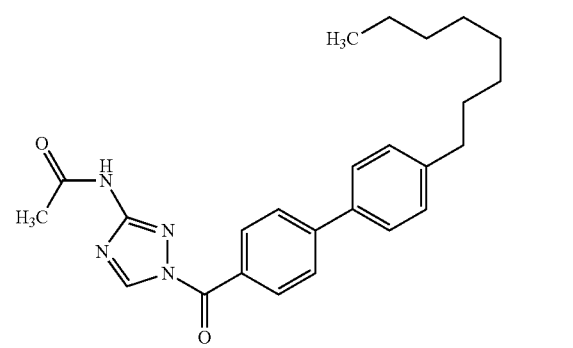
16
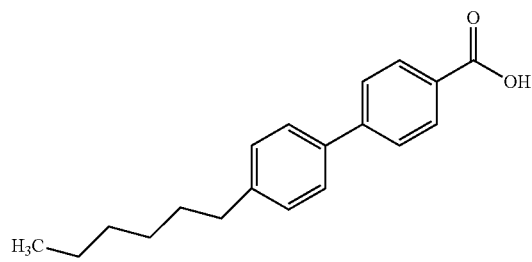
18
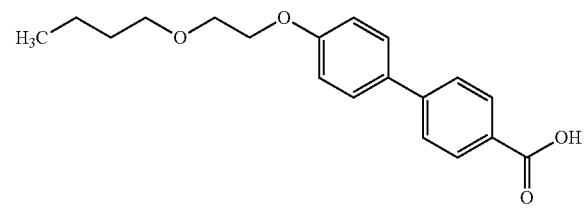
20
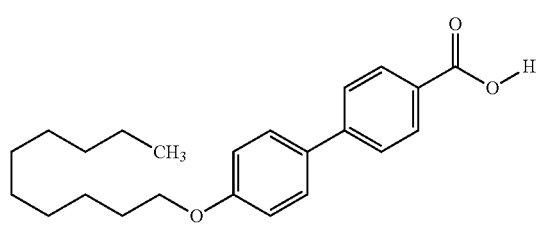
22
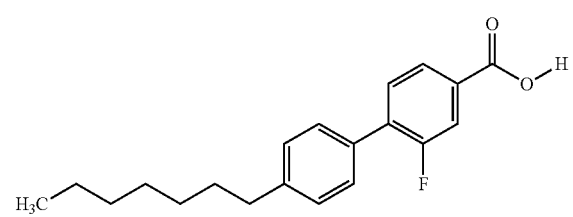

-continued
24
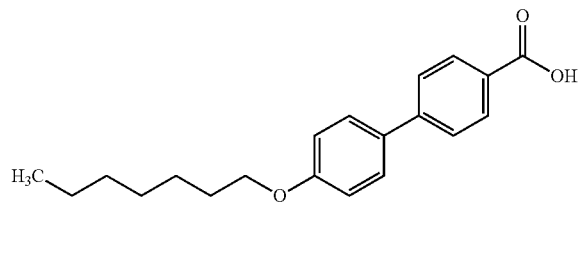
25
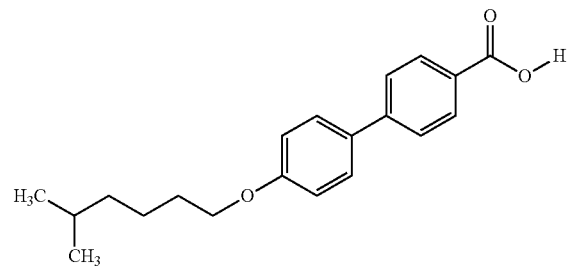
26
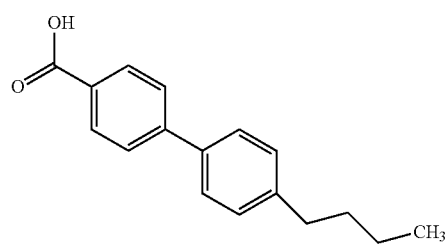
27
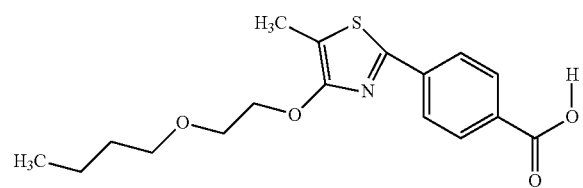
29
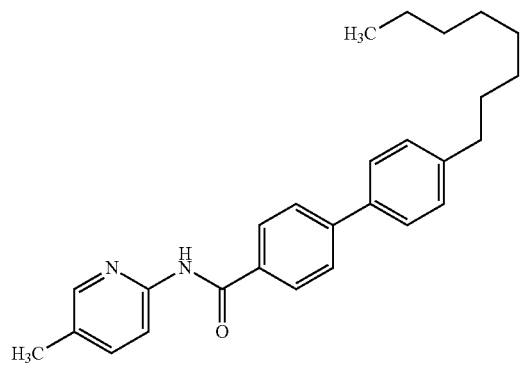
31
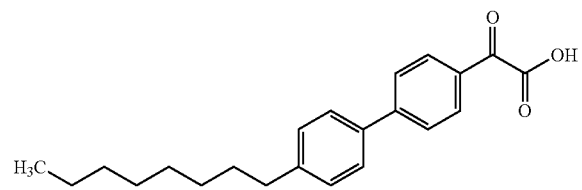
32
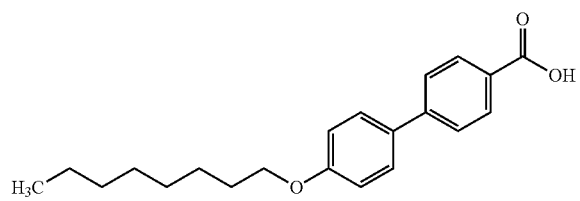
33
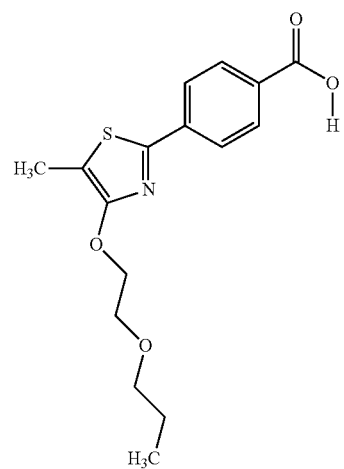

-continued
35
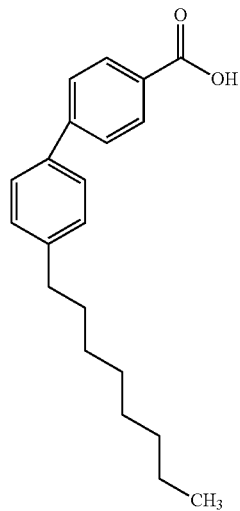
36
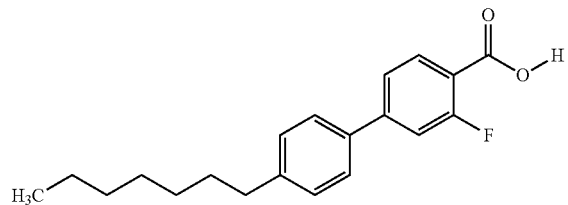
37
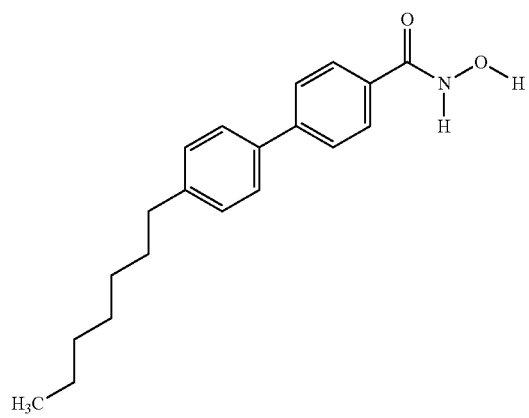
38
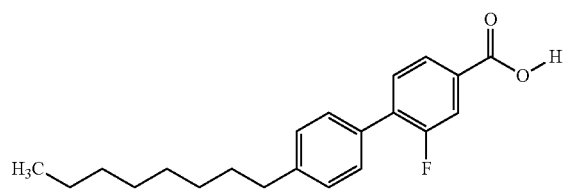
44
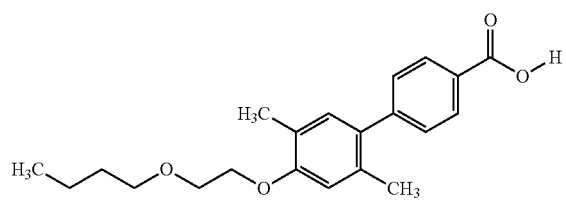
45
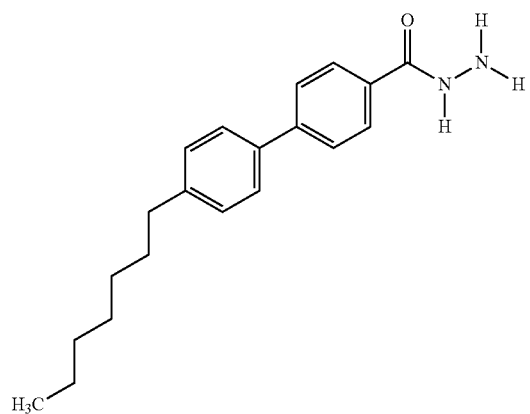

-continued
46
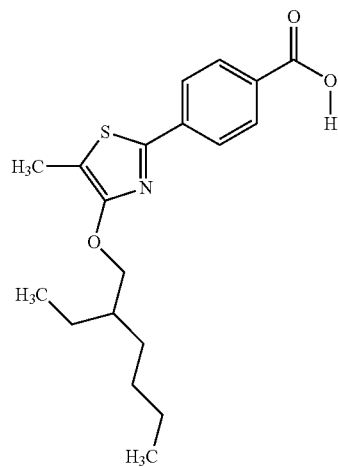
47
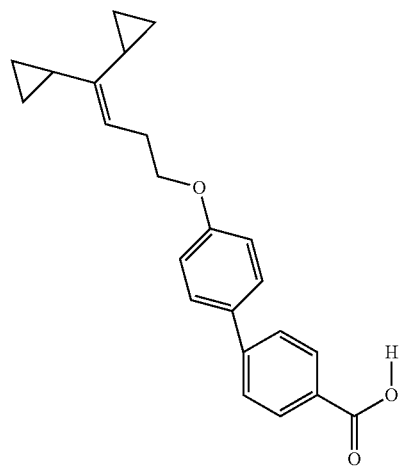
49
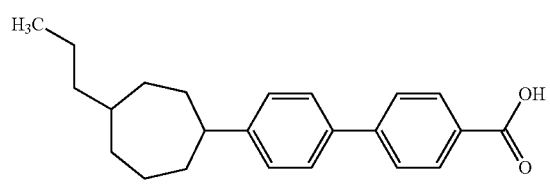
50
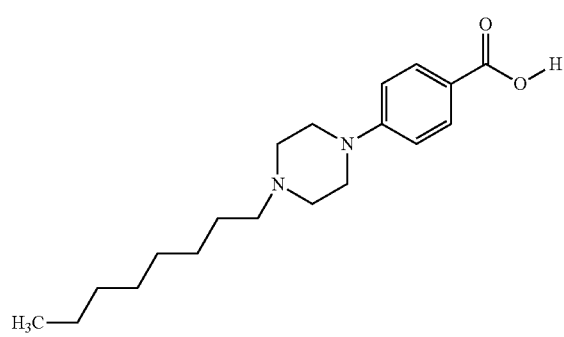
51
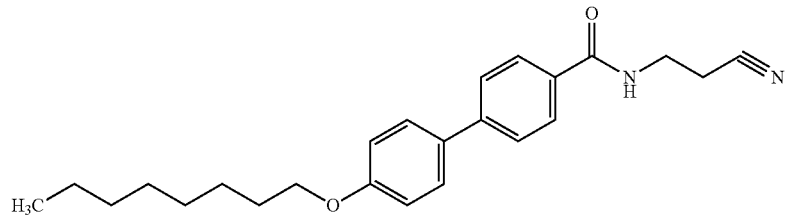
52
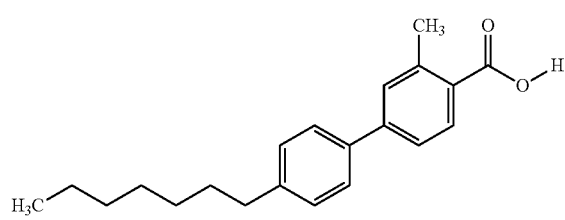
53
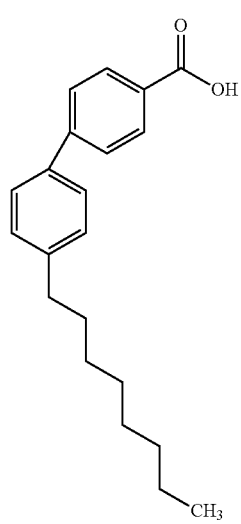

-continued
54
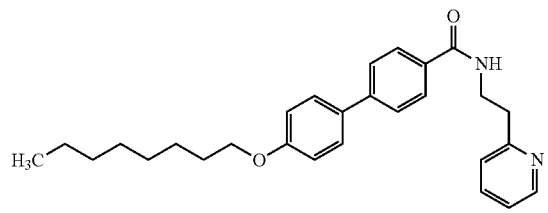
55
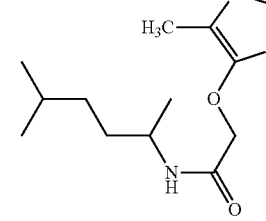
56
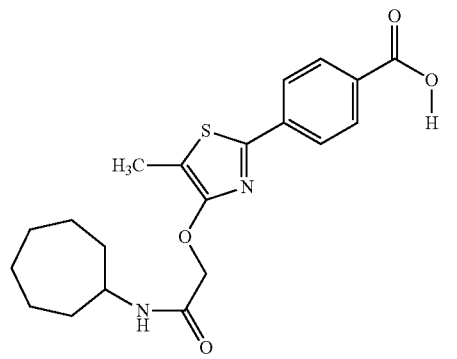
57
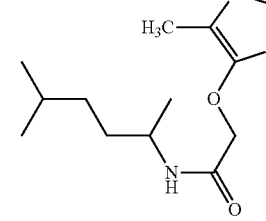
58
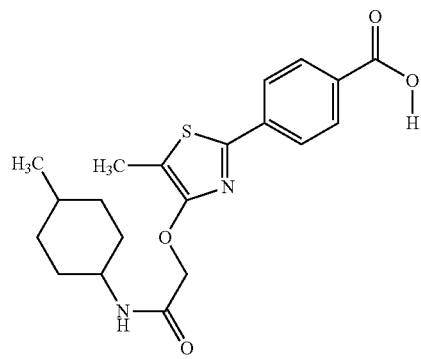
59
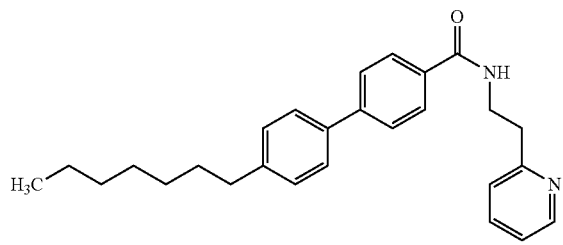
60
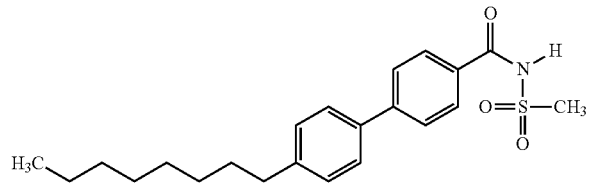
61
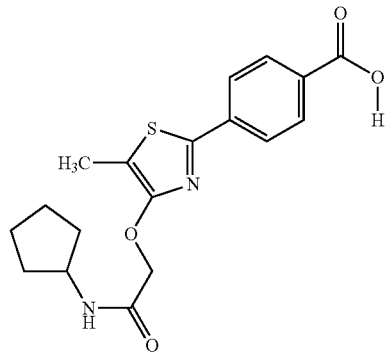

62

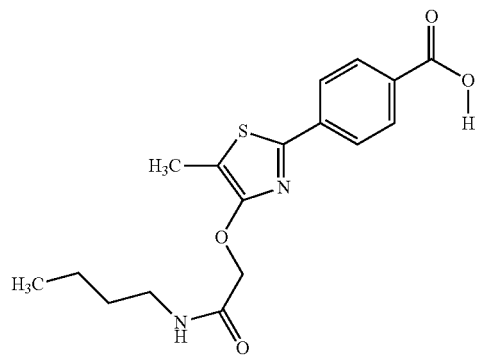

63

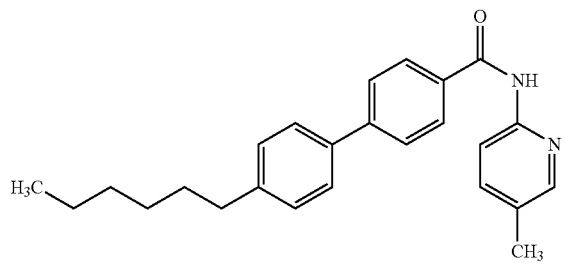

64

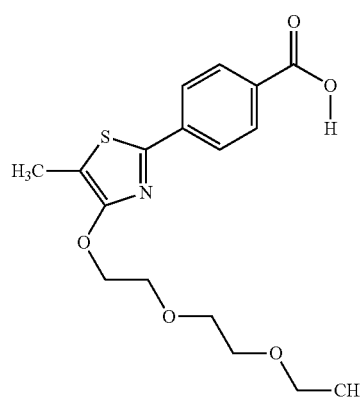

The functional receptor assay, receptor selection and amplification may be performed as described in WO2007/009083, which is incorporated herein by reference in its entirety. For example, Technology (R-SAT) may be used to investigate the pharmacological properties of known and novel RARβ agonists useful for the present invention. R-SAT is disclosed, for example, in U.S. Pat. Nos. 5,707,798, 5,912,132, and 5,955,281, Piu et al., 2006, Beta Arrestin 2 modulates the activity of Nuclear Receptor RARβ2 through activation of ERK2 kinase, Oncogen, 25(2):218-29 and Burstein et al., 2006, Integrative Functional Assays, Chemical Genomics and High Throughput Screening: Harnessing signal transduction pathways to a common HTS readout, Curr Pharm Des, 12(14): 1717-29, all of which are hereby incorporated herein by reference in their entireties, including any drawings.

The relevant RARβ2 receptor modulating activities of the above compounds are described in WO2007/009083, which is incorporated by reference herein in its entirety.

The highly specific RARβ agonist, e.g., AC261066, can prevent hepatic steatosis and activation of HSCs, marked by decreased expression of a-SMA. AC261066 can significantly diminish hepatic gene expression of pro-inflammatory mediators tumor necrosis factor-alpha (TNFα) and monocyte chemotactic protein-1 (MCP-1).

In one aspect, the invention provides a method for producing a cardioprotective effect on a heart of a subject in need thereof, comprising administering to the subject a therapeutically effective amount of a retinoic acid receptor-beta (RARβ) agonist.

In various embodiments, the cardioprotective effect may be an attenuation of an infarct size in the heart. The cardioprotective effect may be a diminution of coronary norepinephrine spillover during reperfusion of the heart. The cardioprotective effect may be an alleviation of reperfusion arrhythmias. As is well-known to one of ordinary skill in the art, the reperfusion arrhythmias may comprise ventricular tachycardia and/or ventricular fibrillation. The ventricular tachycardia and/or ventricular fibrillation may be present when the subject has a heart disease. In certain aspects, the ventricular tachycardia and/or ventricular fibrillation may be present prior to a myocardial infarction in the subject.

In some embodiments, the RARβ agonist may be administered before, during and/or after a myocardial infarction in the subject. The RARβ agonist may be administered chronically in a patient at risk for a myocardial infarction or for a shorter period for a patient at acute risk. Alternatively, the RARβ agonist may be administered during a myocardial infarction in the subject. In certain aspects, the RARβ agonist may be administered after a diagnosis of heart disease in the subject to provide cardioprotection.

In some aspects of the pharmaceutical formulations and methods provided herein, the RARβ agonist may be a synthetic selective retinoic acid β$_2$-receptor (RARβ$_2$) agonist or a pharmaceutically acceptable salt, ester, amide, prodrug thereof, or a combination thereof.

In certain embodiments, the RAR β2 agonist is AC261066 having a structure of Formula 1:

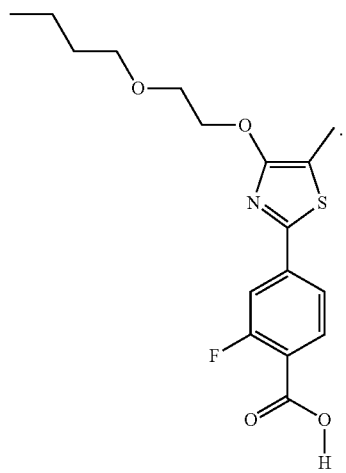

(1)

In other embodiments, the RAR β2 agonist is AC55649 having a structure of Formula 2:

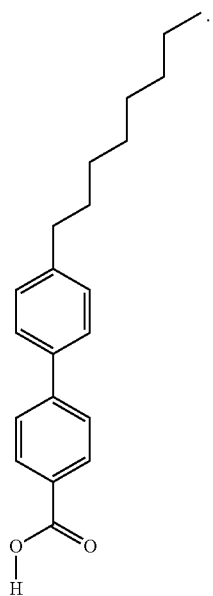

(2)

In alternate embodiments, the RAR β agonist is tazarotene having a structure of Formula 3:

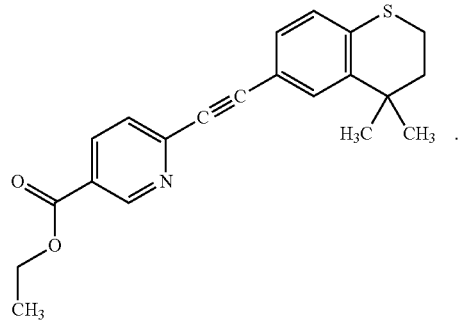

(3)

In another aspect, the RAR β agonist is adapalene having a structure of Formula 4:

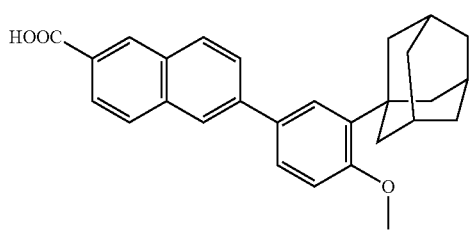

(4)

In yet another aspect, the RAR β agonist is 9-cis-retenoic acid having a structure of Formula 5:

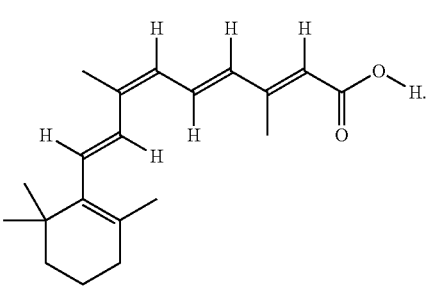

(5)

In still another aspect, the RAR βagonist is 4-[(E)-2-(5,6,7,8-Tetrahydro-5,5,8,8-tetramethyl-2-naphthalenyl)-1-propenyl]benzoic acid (TTNPB) having a structure of Formula 6:

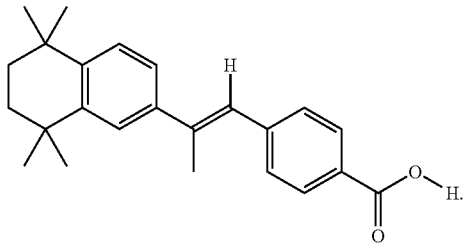

(6)

In certain embodiments, the RARβ agonist may be administered three times daily. In other embodiments, the RARβ agonist may be administered in an amount from about 30 mg to about 200 mg per day.

In other aspects, the RARβ agonist may be administered at a concentration of from about 0.1 mg to about 10 mg per 100 ml. The RARβ agonist also may be administered at a concentration from about 1 mg to about 3 mg per 100 ml.

In various embodiments, the RARβ agonist may be administered orally. Alternatively, the RARβ agonist may be administered parenterally.

Parenteral administration includes intravenous, subcutaneous, sublingual, buccal, nasal, intraarterial, intracardiac, intraarticular, transdermal, transmucosal, intramuscular, intraperitoneal, ophthalmic and/or topical administration.

In other aspects, the presently provided methods further comprise administering to the subject a second therapeutic agent. The second therapeutic agent may be a second retinoic acid receptor-beta (RARβ agonist. The second administered RAR βagonist may be an RAR β₂ agonist, for example, AC261066 having a structure of Formula 1:

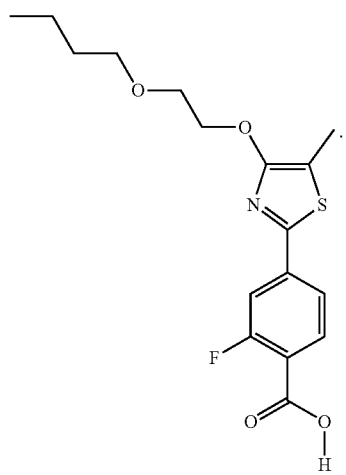

(1)

In an additional embodiment, the second administered RAR βagonist may be an RAR β₂ agonist, for example, AC55649 having a structure of Formula 2:

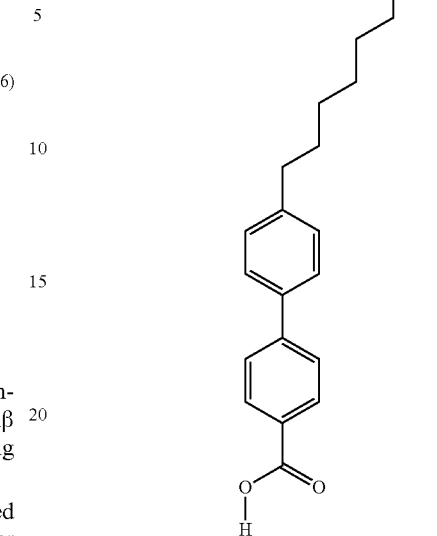

(2)

In another aspect, the invention provides a method for reducing myocardial injury to a heart of a subject in need thereof, comprising administering to the subject a therapeutically effective amount of a retinoic acid receptor-beta (RARβ) agonist. The myocardial injury may be an ischemia/reperfusion (I/R) injury. The I/R injury may be a myocardial infarction. In various aspects, administration of the RARβ agonist reduces the myocardial infarction size. In certain embodiments, the RARβ agonist is a synthetic selective retinoic acid β₂-receptor (RARβ₂) agonist or a pharmaceutically acceptable salt, ester, amide, prodrug thereof, or a combination thereof. The RARβ₂ agonist may have a structure of Formula (1), as shown above. Alternatively, the RARβ₂ agonist may have a structure of Formula (2), as shown above. In additional embodiments, the RARβ agonist may have a structure of any one of Formula (3), Formula (4), Formula (5), or Formula (6), each of which is shown above.

In additional aspects of the method for reducing myocardial injury to a heart of a subject in need thereof, the method further comprises administering to the subject a second therapeutic agent. The second therapeutic agent may be a second retinoic acid receptor-beta (RARβ) agonist, and in particular, the second retinoic acid receptor-beta (RARβ) agonist may be an RARβ₂ agonist having a structure of Formula 1, as shown above, or an RARβ₂ agonist having a structure of Formula 2, as shown above.

In another aspect, the invention provides a method for treating or alleviating chronic arrhythmia or reducing the chance of an arrhythmia occurring in a subject in need thereof, comprising administering to the subject a therapeutically effective amount of a retinoic acid receptor-beta (RARβ) agonist. The RARβ agonist may be a synthetic selective retinoic acid receptor β₂ (RARβ₂) agonist or a pharmaceutically acceptable salt, ester, amide, prodrug thereof, or a combination thereof. More specifically, the RARβ₂ agonist may have may be an RARβ₂ agonist having a structure of Formula 1, as shown above, or an RARβ₂ agonist having a structure of Formula 2, as shown above. In further embodiments, the RARβ agonist may have a structure of any one of Formula (3), Formula (4), Formula (5), or Formula (6), each of which is shown above. In certain aspects of the method for treating or alleviating chronic arrhythmia in a subject in need thereof, the method may further comprise administering to the subject a second therapeutic agent. The second therapeutic agent may be a second retinoic acid receptor-beta (RARβ) agonist, and in particular, the second retinoic acid receptor-beta (RARβ) agonist may be an RARβ$_2$ agonist having a structure of Formula 1, as shown above, or an RARβ$_2$ agonist having a structure of Formula 2, as shown above.

In a further aspect, the invention provides a method for treating cardiac failure in a subject in need thereof, comprising administering to the subject a therapeutically effective amount of a retinoic acid receptor-beta (RARβ) agonist. The RARβ agonist may be a synthetic selective/specific retinoic acid β$_2$-receptor (RARβ) agonist or a pharmaceutically acceptable salt, ester, amide, prodrug thereof, or a combination thereof. More specifically, the RARβ$_2$ agonist may have may be an RARβ$_2$ agonist having a structure of Formula 1, as shown above, or an RARβ$_2$ agonist having a structure of Formula 2, as shown above. In further embodiments, the RARβ agonist may have a structure of any one of Formula (3), Formula (4), Formula (5), or Formula (6), each of which is shown above. In certain aspects of the method for treating cardiac failure in a subject in need thereof, the method may further comprise administering to the subject a second therapeutic agent. The second therapeutic agent may be a second retinoic acid receptor-beta (RARβ) agonist, and in particular, the second retinoic acid receptor-beta (RARβ) agonist may be an RARβ$_2$ agonist having a structure of Formula 1, as shown above, or an RARβ$_2$ agonist having a structure of Formula 2, as shown above.

In another aspect, the invention provides a pharmaceutical formulation comprising a therapeutically effective amount of a retinoic acid receptor-beta (RARβ) agonist and a pharmaceutically acceptable excipient. The RARβ agonist may be a synthetic selective retinoic acid β$_2$ receptor (RARβ$_2$) agonist or a pharmaceutically acceptable salt, ester, amide, prodrug thereof, or a combination thereof. In certain embodiments, the RARβ$_2$ agonist may have a structure of Formula 1, as shown above, or an RARβ$_2$ agonist having a structure of Formula 2, as shown above. In alternate aspects, the RARβ agonist may have a structure of any one of Formula (3), Formula (4), Formula (5), or Formula (6), each of which is shown above.

The pharmaceutical formulation may comprise the RARβ agonist in an amount of from about 30 mg to about 200 mg. In certain aspects, the pharmaceutical formulation may comprise the RARβ agonist in an amount of from about 10 mg to about 100 mg. In various embodiments, the pharmaceutical formulation may comprise the RARβ agonist an amount of from about 10 mg to about 100 mg. Alternatively, the pharmaceutical formulation may comprise the RARβ agonist in an amount of from about 10 mg to about 67 mg. The pharmaceutical formulation may comprise the RARβ agonist in a concentration of from about 0.1 mg to about 10 mg per 100 ml. In other aspects, the pharmaceutical formulation may comprise the RARβ agonist in a concentration from about 1 mg to about 3 mg per 100 ml.

The pharmaceutical formulation comprising the RARβ agonist, in particular, an RARβ$_2$ agonist, may be formulated with a pharmaceutically acceptable excipient for oral administration. In an alternate aspect, the pharmaceutical formulation may be formulated with a pharmaceutically acceptable excipient for parenteral administration. In other aspects, the pharmaceutical formulation may be formulated with a pharmaceutically acceptable excipient for intravenous, subcutaneous, sublingual, buccal, nasal, intraarterial, intracardiac, intraarticular, transdermal, transmucosal, intramuscular, intraperitoneal, ophthalmic or topical administration.

In a further aspect, the invention provides a pharmaceutical formulation comprising a therapeutically effective amount of a retinoic acid receptor-beta (RARβ) agonist and a pharmaceutically acceptable excipient.

As used herein, the term "pharmaceutically acceptable excipient" refers to those excipients which are, within the scope of sound medical judgment, suitable for use in contact with the tissues of humans and lower animals without undue toxicity, irritation, allergic response and the like, and are commensurate with a reasonable benefit/risk ratio.

The term "pharmaceutically acceptable excipient" includes any and all solvents, diluents, and other liquid vehicles, dispersion or suspension aids, surface active agents, isotonic agents, thickening or emulsifying agents, preservatives, solid binders, lubricants and the like, as suited to the particular dosage form desired. Remington: The Science and Practice of Pharmacy, 20th Ed., ed. A. Gennaro, Lippincott Williams & Wilkins, 2000, incorporated herein by reference in its entirety, specifically incorporated by reference in its entirety are disclosures of various excipients and carriers used in formulating pharmaceutically acceptable compositions and known techniques for the preparation thereof.

The pharmaceutical compositions of the invention may be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain excipients, including but not limited to, solvents, diluents, and other liquid vehicles, dispersion or suspension aids, surface active agents, pH modifiers, isotonic agents, thickening or emulsifying agents, stabilizers and preservatives, solid binders, lubricants and the like, as suited to the particular dosage form desired.

The RARβ agonist, and in particular a RARβ$_2$ agonist, may be administered by any method known to one skilled in the art. For example, an RARβ agonist, and in particular a RARβ$_2$ agonist, may be administered orally or parenterally.

The term "parenteral" as used herein includes subcutaneous, intravenous, intramuscular, intra-articular, intra-synovial, intrasternal, intrathecal, intrahepatic, intralesional and intracranial injection or infusion techniques. The pharmaceutical compositions and formulations may be administered orally, intravenously, or subcutaneously. The formulations of the invention may be designed to be short-acting, fast-releasing, or long-acting. Still further, compounds may be administered locally, e.g., intracardially, rather than by systemic means, such as administration (e.g., by injection) to a heart of a subject having ischemia or a myocardial infarction.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers. Besides inert diluents, the oral compositions can also include adjuvants such as wetting agents, emulsifying and suspending agents, sweetening, flavoring, and perfuming agents.

Injectable pharmaceutical formulations comprising an RARβ agonist, specifically an RARβ$_2$ agonist, for example, sterile injectable aqueous or oleaginous suspensions may be formulated according to the known art using suitable dispersing or wetting agents and suspending agents. The sterile injectable pharmaceutical formulation may also be a sterile injectable solution, suspension or emulsion in a nontoxic parenterally acceptable diluent or solvent, for example, as a solution in 1,3-butanediol. Among the pharmaceutically acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil may be employed, including but not limited to, synthetic mono- or diglycerides. In addition, fatty acids such as oleic acid are used in the preparation of injectables.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents such as phosphates or carbonates.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art.

The RARβ agonist, in particular an RARβ$_2$ agonist, of the present invention may be used in combination with a second drug or therapeutic agent, wherein the second drug or second therapeutic agent is administered in a therapeutically effective amount to a subject in need thereof. The second therapeutic agent may be a second retinoic acid receptor-beta (RARβ) agonist. The second drug or therapeutic agent include, but not be limited to, an antiplatelet medication to prevent formation of blood clots in the arteries (such as aspirin, thienopyridines (e.g., clopidogrel or prasugrel is used instead of aspirin in patients who have an aspirin allergy), and the glycoprotein IIb/IIIa inhibitors), an anticoagulant medication to prevent growth of blood clots in the arteries (such as intravenous or subcutaneous heparin, subcutaneous low molecular weight heparin, and oral warfarin (Coumadin) or direct thrombin inhibitors (e.g., rivaroxaban (Xarelto) and dabigatran (Pradaxa)), clot-dissolving medications to open blocked arteries (such as fibrinolytic or thrombolytic medications, (e.g., intravenous administration of tissue plasminogen activator (TPA) or TNK, which can open up to 80% of acutely blocked coronary arteries)), medications to decrease the need for oxygen by the heart's muscle (such as nitroglycerine, which dilates coronary arteries), medications to prevent abnormal heart rhythms (such as antiarrhythmic drugs (e.g., amiodarone, and lidocaine) or beta blockers for tachycardia (e.g., acebutol and propranolol)) or a combination thereof when medically advisable in the professional judgement of one ordinarily skilled in the art of treating and/or preventing ischemia and myocardial infarctions.

Additional treatment may include coronary angiography with either percutaneous transluminal coronary angioplasty (PTCA) with or without stenting to open blocked coronary arteries. Supplemental oxygen may be administered to the subject to increase the supply of oxygen to the heart's muscle.

All patents and literature references cited in the present specification are hereby incorporated by reference in their entirety.

EXAMPLES

Example 1

Methods for Examples

I/R in Ex-Vivo Mouse Hearts

Wild type (WT) C57/BL6 and ApoE$^{-/-}$ male mice (C57/BL6 background, from Jackson Labs, Bar Harbor, Me.) were maintained on a regular laboratory chow diet (Con diet, #5053, Pico Diet, PicoLab Rodent Diet, LabDiet, St. Louis, Mo.). Six weeks after birth, another group of ApoE$^{-/-}$ mice received, in addition to their chow diet, drinking water containing 3.0 mg AC261066/100 ml in 0.1% DMSO/H$_2$O for 6 weeks. Twenty minutes after a heparin injection (100 I.U., i.p.) to avoid blood clotting, mice were anesthetized with CO$_2$ vapor and humanely killed by cervical dislocation while under anesthesia (Institutional Animal Care and Use Committee approved). Hearts were quickly excised and cooled in ice-cold Krebs-Henseleit (KH) solution (composition, mM: NaCl 120; KCl 4.71; CaCl$_2$ 2.5; MgSO$_4$ 1.2; KH$_2$PO$_4$ 1.2; NaHCO$_3$ 84.01; Dextrose 11.1; Pyruvic acid 2.0; EDTA 0.5), equilibrated with 95% O$_2$+5% CO$_2$. Hearts were then cannulated via the aorta with a 20-gauge needle and perfused in a Langendorff apparatus (Radnoti, Monrovia, Calif.) at constant pressure (100 cm H$_2$O) with KH solution at 37° C. Two needle electrodes were attached to the surface of the right atrium and left ventricular apex for ECG recordings. ECG was recorded online (sample frequency of 1 kHz) and arrhythmia duration was analyzed using Powerlab/8SP (ADInstruments, Colo. Springs, Colo.). Following a 20-minute stabilization, all hearts were subjected to 40-minute normothermic global ischemia, induced by complete cessation of coronary perfusion, followed by 120-minute reoxygenation (reperfusion) with KH solution (I/R). I/R-injured areas (i.e., infarct size) were analyzed at the end of reperfusion. Coronary flow was measured by timed collections of the effluent every 2 minutes, and samples were assayed for norepinephrine (NE) by high-performance liquid chromatography with electrochemical detection as previously described.

Experiments were also performed on WT C57/BL6 mice, maintained on either a standard laboratory chow (Control diet) (#5053, Pico Diet) or a high-fat diet (HFD) with 45% kcal from fat, (#58125, Test Diet) for 3-5 months. Six weeks after the start of the HFD, these mice received either drinking water containing 0.1% DMSO (vehicle) or water/0.1% DMSO containing AC261066 (3.0 mg/100 ml). As powder, AC261066 is stable at room temperature, according to the manufacturer. The HPLC results showed that AC261066 is stable in the drinking water for at least one week at room temperature. The half-life in the heart is not known. The scientist performing the ex-vivo I/R procedure was blinded to the identities of the groups of mice.

TTC Staining for Ischemic Area in Mouse Hearts

At the end of 120-minute reperfusion, hearts were cut (6-7 sections/heart, 2-mm thick), incubated in an aqueous solution of 2,3,5-triphenyltetrazolium chloride (1% w/v) (TTC, Sigma-Aldrich, St. Louis, Mo.) for 20 minutes at 37° C., and transferred to a formaldehyde solution (10% v/v) for overnight fixation. Heart slices were photographed with a 16× magnification and analyzed by computerized morphometry using Image J software (NIH) to measure infarct sizes (expressed as percentage of ischemic vs. total left ventricular area). Infarct size was measured in every slice and then averaged for each single heart. The most representative sections were chosen for illustration.

Malondialdehyde (MDA) Staining

Cryo-Sectioning.

At the end of I/R, mouse hearts were fixed in 4% paraformaldehyde in PBS overnight at 4° C., and then incubated in 30% sucrose in PBS overnight at 4° C. Tissues were embedded in optimal cutting temperature (OCT) compound and subjected to cryo-sectioning. The sections were 15-µm thick and stored at −80° C. prior to immunostaining.

Immunostaining.

Frozen sections were dried at room temperature before staining. Briefly, the sections were washed in PBS, blocked in 10% goat serum plus 0.02% Triton X-100 in PBS for 30 minutes at room temperature, followed by incubation with an anti-malondialdehyde (MDA) antibody (1:200, Abcam, cat #6463, lot #GR3191333-3, Cambridge, Mass.) overnight at 4° C. Sections were then incubated with a goat anti-rabbit IgG secondary antibody at room temperature for 1 hour (cat #B40962, ready to use, Thermo Fisher Scientific, Eugene, Oreg.). As a negative control, sections were stained without incubation with the primary antibody. Signals were visualized based on a peroxidase-detection mechanism with 3,3-diaminobenzidine (DAB) (Product #34002, Thermo Fisher Scientific, Rockford, Ill.) used as the substrate. Six to eight representative areas of each heart section from 3-4 mice per group were photographed and analyzed.

Toluidine Blue Staining of Mast Cells (MC)

At the end of 120-minute reperfusion, hearts were cut and processed for frozen sections. Heart sections (15-µm thick) were stained with toluidine blue (0.5%) to visualize MC under transmitted light. MC were identified with a 60× magnification. Intact and degranulated MC were counted in the analyzed sections, and MC degranulation was calculated as a percentage of degranulated MC over total MC. Three sections of each heart from 3-4 mice per group were analyzed.

Lipid Panel Measurements

Lipid panel measurements were carried out using the CardioChek® PA analyzer (PTS Diagnostics, Indianapolis, Ind.). Briefly, 40 µl of mouse tail blood were applied to test strips to measure the levels of total cholesterol, high-density lipoprotein (HDL) cholesterol, low-density lipoprotein (LDL) cholesterol, and triglycerides. Statistical differences among the groups were calculated using one-way analysis of variance (ANOVA), followed by the Bonferroni Correction for post hoc analysis.

Statistical Analysis of Data

Statistical analysis was performed with GraphPad Prism 7.0 software (San Diego, Calif., USA). All data are reported as means±SEM. Statistical analysis was performed only when a minimum of n=5 independent samples was acquired, and was performed with unpaired t-test when comparing two different groups and with one-way ANOVA followed by Dunnett's post-hoc test when comparing more than two groups of data. Data and statistical analysis comply with the recommendations on experimental design and analysis in Pharmacology. Data were considered statistically significant when a value of at least p<0.05 was achieved.

Example 2

The RARβ2 Agonist AC261066 Decreases NE Overflows, Reperfusion Arrhythmias and Infarct Sizes in Murine ApoE$^{-/-}$ Hearts Subjected to Ex-Vivo I/R Since high blood cholesterol levels are a major factor in myocardial ischemia, first investigated was whether the RARβ$_2$ agonist AC261066 influences relevant parameters of I/R-induced cardiac dysfunction, such as NE release, arrhythmia severity, and infarct size in hypercholesterolemic ApoE$^{-/-}$ mice. For this, spontaneously beating Langendorff-perfused mouse hearts were subjected to 40-minute global ischemia followed by 120-minute reperfusion (I/R). In control WT hearts, it was found that NE overflows during reperfusion amounted to ~80 pmol/g, ventricular arrhythmias (tachycardia and fibrillation, VT/VF) lasted 50 seconds, and infarct sizes comprised ~25% of the left ventricle. In ApoE$^{-/-}$ hearts subjected to I/R, NE overflows, VT/VF durations and infarct sizes were each ~60% greater than in WT hearts. Notably, in hearts from ApoE$^{-/-}$ mice treated orally for 6 weeks with AC261066 and then subjected to I/R ex vivo in the absence of AC261066, NE overflows, VT/VF durations, and infarct sizes were markedly reduced by ~35-45% as compared to those in untreated ApoE$^{-/-}$ hearts subjected to I/R (FIG. 1). Notably, coronary flow in ApoE$^{-/-}$ hearts (3.025±0.46 ml/min) did not differ from that of ApoE$^{-/-}$ hearts treated with AC261066 (2.092±0.25 ml/min). These findings suggest that signaling via RARβ$_2$ exerts protective effects in a genetic hypercholesterolemic ex-vivo I/R heart model.

Example 3

Figures 2A, 2B:
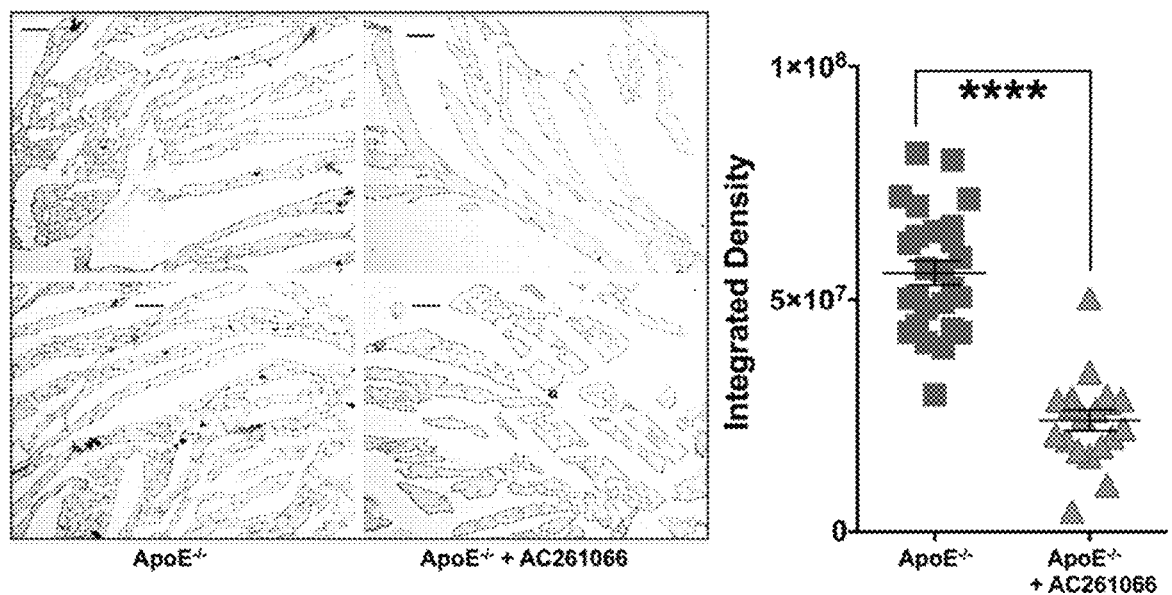
FIGS. 2(A)-2(B) illustrates malondialdehyde (MDA) levels in heart sections of ApoE$^{-/-}$ mice, either untreated or treated with AC261066, subjected to ex-vivo I/R. Following I/R, hearts were fixed, embedded in optimal cutting temperature (OCT) compound, and sectioned. Sections were stained with an MDA antibody (Magnification: 200×), red arrow marks MDA signal.

The RARβ$_2$Agonist AC261066 Limits the Increase in Oxidative Stress in Murine ApoE$^{-/-}$ Hearts Subjected to Ex-Vivo I/R Since the hearts from mice treated orally with AC261066 displayed protective features in this ex-vivo hypercholesterolemic I/R model in the absence of AC261066 in vitro, the inventors questioned whether these cardioprotective effects resulted from an attenuation of I/R-induced oxidative stress. Accordingly, whether the RARβ$_2$ agonist AC261066 influences the production of malondialdehyde (MDA), a classical marker of oxidative stress, was investigated. It was found that a 6-week oral treatment with AC261066 markedly reduced the level of MDA in hearts from ApoE$^{-/-}$ mice subjected to I/R as compared to their untreated controls; this reduction amounted to ~60% (FIG. 2). These findings suggested that the protective effects provided by the drug AC261066 in ApoE$^{-/-}$ hearts likely result at least in part from a reduction in I/R-induced oxidative stress.

Example 4

Figures 3A, 3B:
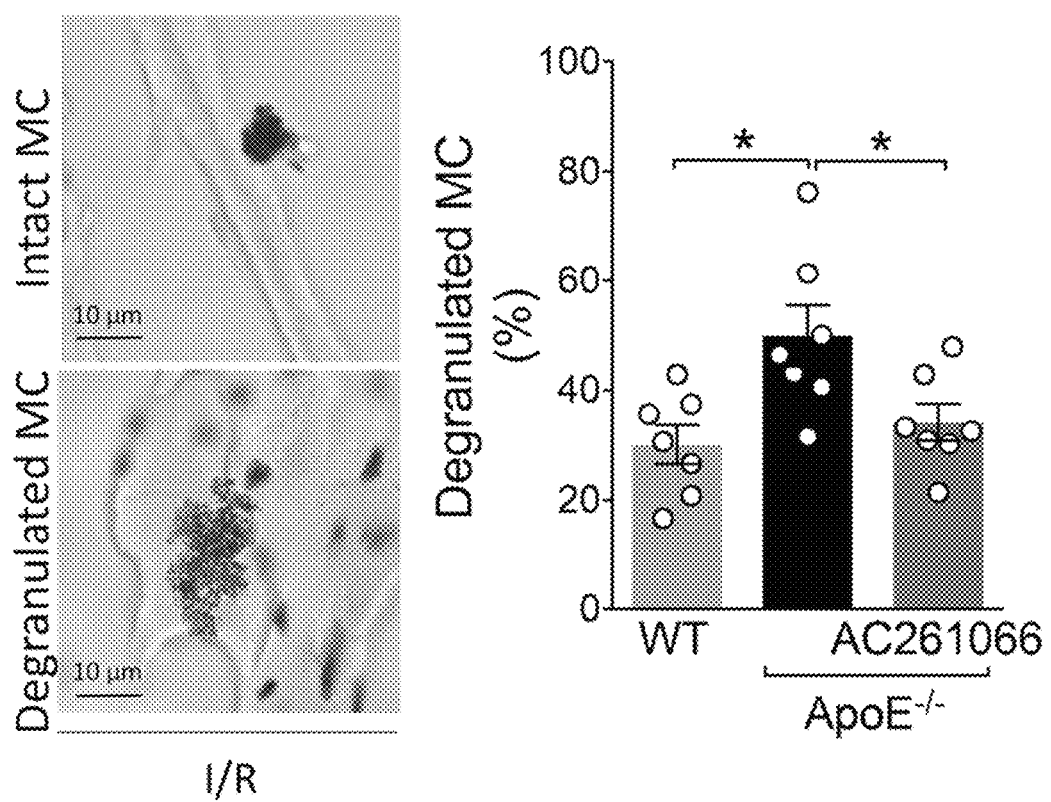
FIGS. 3(A)-3(B) show that the RARβ$_2$ agonist AC261066 reduces mast cell degranulation in ApoE$^{-/-}$ mouse hearts subjected to ex-vivo I/R. Frozen heart sections of WT, ApoE$^{-/-}$ and ApoE$^{-/-}$+AC2610166 mouse hearts subjected to I/R (n=7, 7, 7) were stained with toluidine blue.

The RARβ$_2$Agonist AC261066 Reduces Mast Cell (MC) Degranulation in Murine ApoE$^{-/-}$ Hearts Subjected to Ex-Vivo I/R I/R-induced cardiac dysfunction is known to be associated with local MC degranulation and consequent release of noxious mediators, elicited by toxic aldehydes produced in the setting of oxidative stress (Koda et al., 2010). Thus, whether the cardioprotection afforded by AC261066 in I/R is accompanied by a reduction in MC degranulation we determined. Frozen sections of WT, ApoE$^{-/-}$ and AC261066-treated ApoE$^{-/-}$ murine hearts subjected to I/R were stained with toluidine blue to identify MC and assess their degranulation. We found that in hearts from WT mice, I/R elicited MC degranulation which amounted to ~30% of the total MC number. In hearts from ApoE$^{-/-}$ mice, I/R-induced MC degranulation increased to ~50%, but in AC261066-treated ApoE$^{-/-}$ hearts I/R-induced MC degranulation was reduced by ~30% as compared to that in untreated ApoE$^{-/-}$ hearts (FIG. 3). These data indicate that the protective effects provided by AC261066 in ApoE$^{-/-}$ hearts subjected to ex-vivo I/R may result from a decrease in MC degranulation elicited by products of oxidative stress.

Example 5

Figures 4A, 4B, 4C:
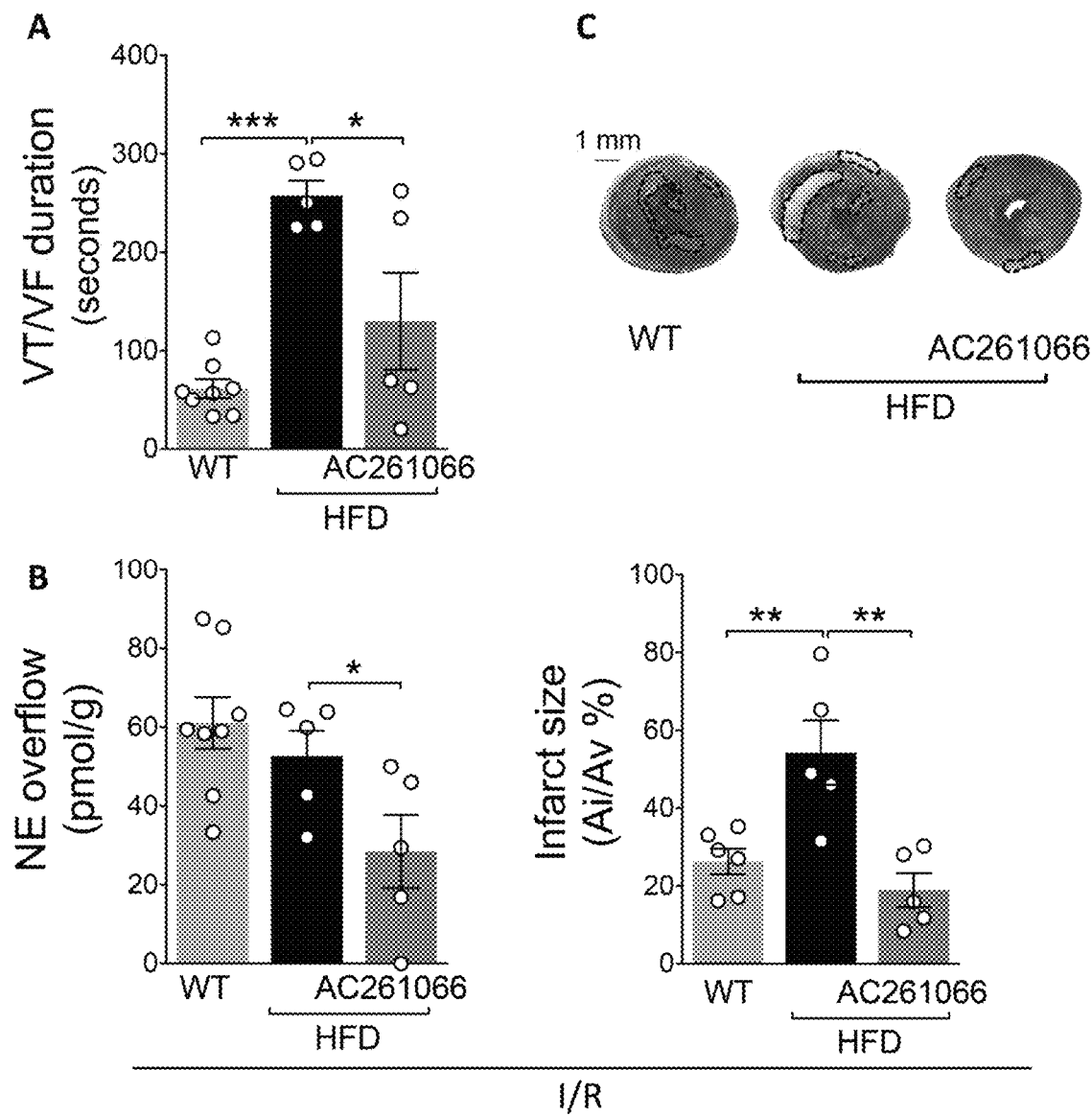
FIGS. 4(A)-4(C) illustrate that the RARβ$_2$ agonist AC261066 reduces NE overflows, alleviates reperfusion arrhythmias and decreases infarct sizes in hearts from HFD-fed mice subjected to ex-vivo I/R. Mouse hearts were subjected to 40-minute global ischemia followed by 120-minute reperfusion (WT, n=8; HFD, n=5, HFD+AC261066, n=5).

The RARβ$_2$Agonist AC261066 Decreases NE Overflows, Reperfusion Arrhythmias, and Infarct Sizes in HFD-Fed Murine Hearts Subjected to Ex-Vivo I/R The present studies with ApoE$^{-/-}$ mice indicated that AC261066 exerts cardioprotective anti-I/R effects. Therefore, we next investigated whether cardioprotection also occurs in hearts from WT C57BL6 mice fed a high-fat diet (HFD), which is known to enhance oxidative stress and cause cardiac dysfunction (Zeng et al., 2015). For this testing, spontaneously beating, Langendorff-perfused hearts from chow, HFD- and HFD+AC261066-fed mice were subjected to 40-minute global ischemia followed by 120-minute reperfusion (I/R). In hearts from chow-fed mice, NE overflows during reperfusion amounted to ~60 pmol/g, ventricular arrhythmias (tachycardia and fibrillation, VT/VF) lasted ~60 seconds, and infarct sizes comprised ~25% of left ventricles (FIG. 4). In hearts from HFD-fed mice subjected to I/R, NE overflows were as large as in hearts from chow-fed WT, and VT/VF durations and infarct sizes were ~4- and 2-fold greater than in chow-fed WT hearts. In hearts from HFD-fed mice treated orally with AC261066 prior to ex-vivo I/R, NE overflows, VT/VF durations, and infarct sizes were markedly reduced by ~45-65% as compared with those in untreated HFD hearts (FIG. 4). Notably, coronary flow in HFD hearts (3.02±0.19 ml/min) did not differ from that of HFD hearts treated with AC261066 (3.015±0.27 ml/min). Thus, the RARβ$_2$ agonist AC261066 also displays protective effects in a non-genetic, obese mouse ex-vivo I/R heart model.

Example 6

Figures 5A, 5B:
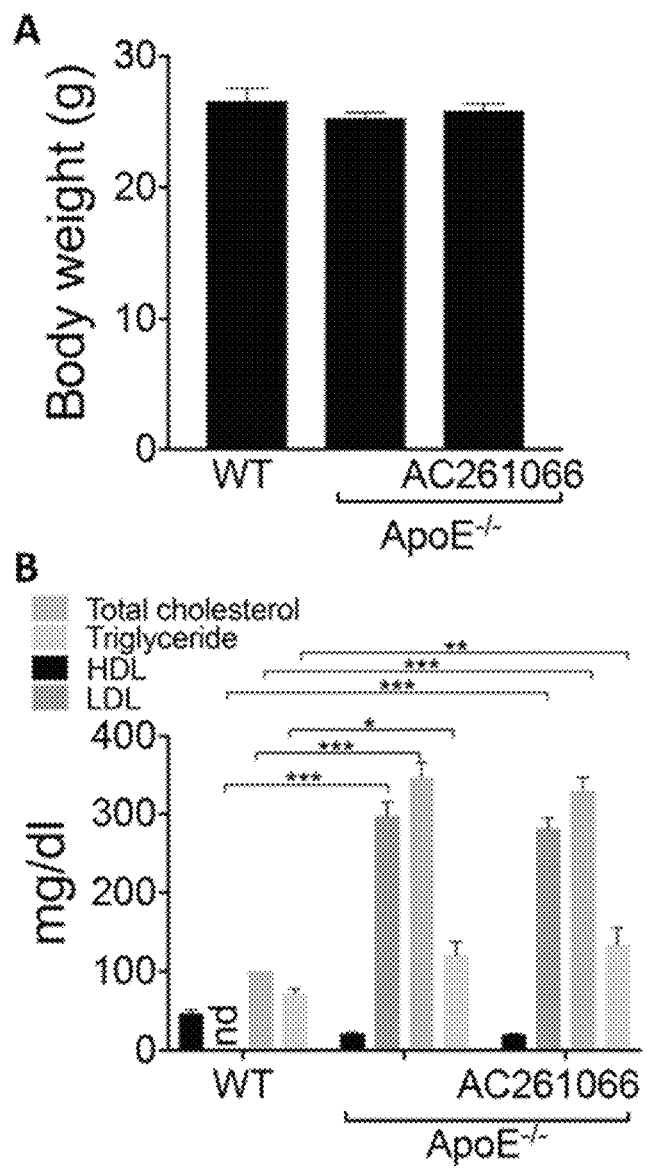
FIGS. 5(A)-5(B) graphically illustrate that body weight and total cholesterol levels of ApoE$^{-/-}$ mice are not affected by the RARβ$_2$ agonist AC261066.

Oral AC261066 Treatment does not Reduce Total Cholesterol, Triglyceride, HDL and LDL Blood Levels in ApoE$^{-/-}$ Mice There were no significant differences in body weight among WT, ApoE$^{-/-}$ and ApoE$^{-/-}$ mice treated orally with AC261066 (FIG. 5, panel A). Total cholesterol, triglycerides, HDL, and LDL blood levels were markedly increased in ApoE$^{-/-}$ mice as compared with WT controls, whereas HDL levels were slightly reduced in ApoE$^{-/-}$ and AC261066-treated ApoE$^{-/-}$ mice when compared to WT. Most importantly, oral treatment of ApoE$^{-/-}$ mice with AC261066 did not modify total cholesterol, triglycerides, HDL and LDL blood levels (FIG. 5, panel B), indicating that the blood lipid profile does not play a major role in the cardioprotective effects of this RARβ$_2$ selective agonist.

The purpose of the present examples was to characterize the effects of a RARβ$_2$-selective, synthetic agonist, AC261066, in an ex-vivo I/R injury model in the heart. The inventors chose to test the effects of AC261066 in two dysmetabolic murine models because hyperlipidemic states are known to be causally associated with myocardial ischemia and oxidative stress, and also because it was previously discovered that AC261066 decreases oxidative stress in the liver, pancreas and kidneys of HFD-fed mice. The inventors found that a 6-week oral treatment with AC261066 in both genetically hypercholesterolemic (ApoE$^{-/-}$) and obese (HFD-fed) mice exerts protective effects when their hearts are subsequently subjected to I/R ex vivo in the absence of added drug. Most importantly, this cardioprotection ensued without any major changes in the hyperlipidemic state, indicating that the cardioprotective effects of this RARβ$_2$ selective agonist do not derive from hypothetical modification of the blood lipid profile (see FIG. 5). Furthermore, although RAR and RXR activation has been shown to relax resistance vessels via the endothelium-dependent NO-cGMP pathway, AC261066-induced cardioprotection was not associated with an increase in coronary flow, since treatment with AC261066 did not modify coronary flow in hearts from ApoE$^{-/-}$ and HFD-fed mice.

Langendorff-perfused mouse hearts subjected to I/R undergo a sizeable infarct of the left ventricle. A prominent characteristic of AC261066-afforded protection in our ex-vivo heart model was the reduction in I/R-induced infarct size in the hearts of both ApoE$^{-/-}$ and HFD-fed WT mice. In as much as the extent of myocardial injury associated with I/R results at least in part from oxidative stress and formation of toxic aldehydes, the inventors measured MDA levels, a known maker of oxidative stress, in post-I/R hearts, and found them to be significantly reduced in sections from AC261066-treated ApoE$^{-/-}$ as compared with untreated ApoE$^{-/-}$ control mice. Accordingly, this RARβ$_2$-selective agonist most likely reduces I/R-induced oxidative stress and thus, infarct size. Since the production of oxygen radicals and toxic aldehydes occurs primarily at the cardiomyocyte mitochondrial level, it is believed that intranuclear RARβ$_2$ activation recruits a yet-to-be uncovered signaling pathway which ultimately results in oxidative stress reduction. The AC261066-induced reduction in infarct size results from a decrease in apoptosis, favored by the reduction in oxidative stress, or involves other protective mechanisms.

Cardiac I/R is accompanied by systemic and local sympathetic neural activation, which characteristically results in abundant NE release in the heart. I/R-induced activation of a local renin-angiotensin system (RAS) is a major contributor to this enhancement of NE release. The inventors found that NE coronary spillover was significantly increased during reperfusion in chow- and HFD-fed hearts, as well as in WT and ApoE$^{-/-}$ hearts. A novel finding of the inventors was that oral treatment with AC261066 markedly curtailed I/R-induced NE overflow in the hearts from both ApoE$^{-/-}$ and HFD-fed mice. Although it has not been previously demonstrated, it is plausible that RARβ$_2$ activation directly interferes with NE exocytosis from sympathetic nerve endings. Yet, a major mechanism of this protective effect probably derives from a diminished activation of local cardiac RAS, likely a result of the decreased MC degranulation also elicited by AC261066 treatment. Indeed, enzymatically active renin is present in cardiac MC, and renin release during I/R constitutes the first step of local RAS activation that culminates in angiotensin-induced cardiac dysfunction, including excessive NE release.

While not intending to be bound by any particular mechanism of operation, it is believed that the reduction in NE release which occurred in the hearts of AC261066-treated mice also contributed to the decrease in infarct size. Indeed, I/R-induced cardiac injury is known to be enhanced by the vasoconstriction and increased oxygen demand associated with hyperadrenergic states. Concomitantly, RAS activation and increased angiotensin production likely contributed to the enhancement of cardiac injury, given the recognized capacity of angiotensin to promote the formation of oxygen radicals.

Whether AC261066 treatment decreased the I/R-induced degranulation of cardiac MC by one or more mechanisms directly involving MC exocytotic pathways remains to be determined. Nonetheless, given the well-known capability of oxygen radicals and toxic aldehydes to degranulate MC, while not intending to be bound by any particular mechanism of operation, it is believed that the AC261066-induced reduction in MC degranulation results from the attenuation of oxidative stress and toxic aldehyde formation by this selective RAR$\beta_2$ agonist.

Preeminent in the cardioprotective effects of AC261066 in our ex-vivo murine I/R model was an alleviation of reperfusion arrhythmias, characterized by an abbreviation of ventricular tachycardia and fibrillation. Given the notorious arrhythmogenic effects of catecholamines, it is likely that the attenuation of NE release from I/R hearts of the AC261066-treated mice played a major role in the anti-arrhythmic effects of AC261066. At the same time, since oxygen radicals are known to elicit cardiac arrhythmias by multiple mechanisms, it is likely that the AC261066-induced reduction in oxidative stress contributed to the alleviation of reperfusion arrhythmias. In addition, since angiotensin is highly arrhythmogenic, both directly and via oxygen radical production, the AC261066-induced reduction of MC degranulation, and thus of renin release and RAS activation, is likely to have contributed to its anti-arrhythmic effects.

In conclusion, treatment of mice with the selective RAR$\beta_2$ agonist AC261066 afforded cardioprotection in their ex-vivo hearts subjected to I/R. Cardioprotection consisted of an attenuation of infarct size, diminution of NE spillover, and alleviation of reperfusion arrhythmias. This cardioprotection was associated with a reduction in oxidative stress and MC degranulation.

Figure 6:
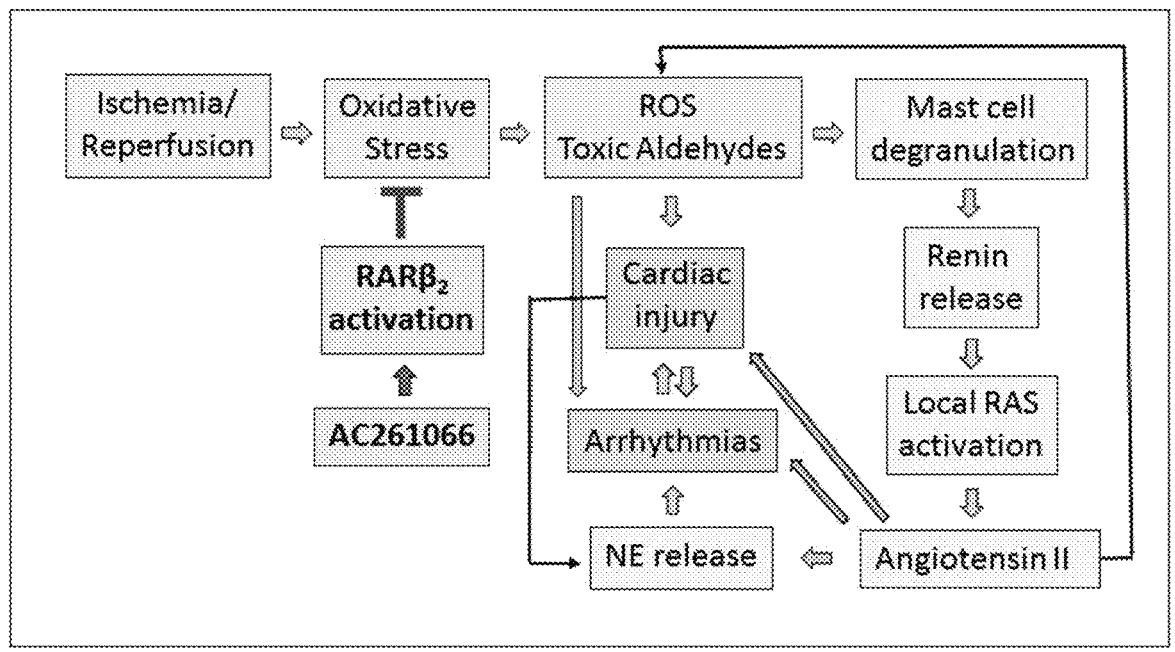
FIG. 6 depicts a proposed mechanism for the cardioprotective effect of AC261066.

While not intending to be bound by any particular mechanism of operation, it is believed that the reduction in myocardial injury and adrenergic activation, as well as the antiarrhythmic effects, result at least in part from decreased formation of oxygen radicals and toxic aldehydes known to elicit the release of MC-derived renin, promoting the activation of local RAS leading to enhanced NE release and reperfusion arrhythmias (FIG. 6). In as much as these beneficial effects of AC261066 occurred at the ex-vivo level following oral drug treatment, the present data show that AC261066 is not only as a drug to reduce I/R injury of the heart, but also a drug for patients affected by other cardiovascular ailments, such as chronic arrhythmias and cardiac failure.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A method for providing a cardioprotective effect on a heart of a subject in need thereof, comprising administering to the subject a therapeutically effective amount of a retinoic acid receptor-beta (RAR$\beta$) agonist, wherein the RAR$\beta$ agonist is AC261066 having a structure of Formula 1:

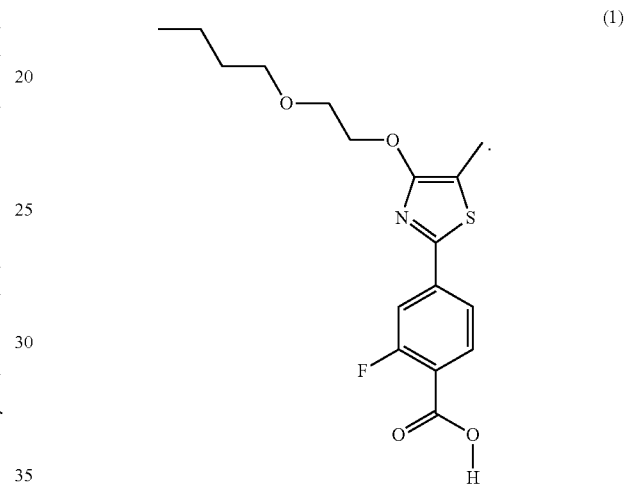

or the RAR$\beta$ agonist is AC55649 having a structure of Formula 2:

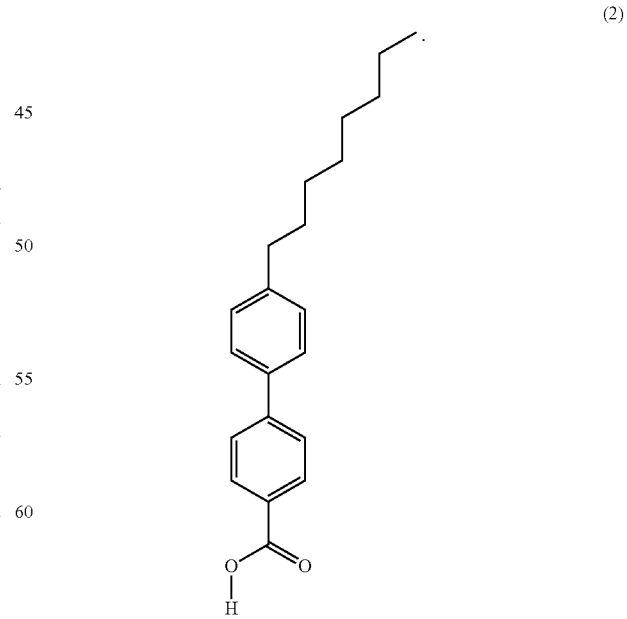

2. The method of claim 1, wherein the cardioprotective effect is an attenuation of an infarct size in the heart.

3. The method of claim 1, wherein the cardioprotective effect is a diminution of coronary norepinephrine spillover during reperfusion of the heart.

4. The method of claim 1, wherein the cardioprotective effect is an alleviation of reperfusion arrhythmias.

5. The method of claim 1, wherein the reperfusion arrhythmias comprise ventricular tachycardia and/or ventricular fibrillation.

6. The method of claim 5, wherein the ventricular tachycardia or ventricular fibrillation is present when the subject has a heart disease.

7. The method of claim 5, wherein the ventricular tachycardia or ventricular fibrillation is present prior to a myocardial infarction in the subject.

8. The method of claim 1, wherein the RARβ agonist is administered before, during and/or after a myocardial infarction in the subject.

9. The method of claim 1, wherein the RARβ agonist is administered chronically for a long term or acutely for a short term.

10. The method of claim 1, wherein the RARβ agonist is administered during a myocardial infarction in the subject.

11. The method of claim 1, wherein the RARβ agonist is administered after a diagnosis of heart disease in the subject.

12. The method of claim 1, wherein the RARβ agonist is a synthetic selective retinoic acid $\beta_2$-receptor (RAR$\beta_2$) agonist or a pharmaceutically acceptable salt, ester, amide, prodrug thereof, or a combination thereof.

13. The method of claim 1, wherein said administration is oral, intravenous, subcutaneous, sublingual, buccal, nasal, intraarterial, intracardiac, intraarticular, transdermal, transmucosal, intramuscular, intraperitoneal, ophthalmic, or topical administration, or a combination thereof.

* * * * *